(12) United States Patent
Cunningham

(10) Patent No.: US 8,303,582 B2
(45) Date of Patent: Nov. 6, 2012

(54) ELECTROSURGICAL INSTRUMENT HAVING A COATED ELECTRODE UTILIZING AN ATOMIC LAYER DEPOSITION TECHNIQUE

(75) Inventor: James S. Cunningham, Boulder, CO (US)

(73) Assignee: TYCO Healthcare Group LP, Mansfield, MA (US)

( * ) Notice: Subject to any disclaimer, the term of this patent is extended or adjusted under 35 U.S.C. 154(b) by 1052 days.

(21) Appl. No.: 12/210,598

(22) Filed: Sep. 15, 2008

(65) Prior Publication Data
US 2010/0069904 A1    Mar. 18, 2010

(51) Int. Cl.
*A61B 18/18* (2006.01)
(52) U.S. Cl. .......................................... 606/48; 606/51
(58) Field of Classification Search ................ 606/45–52
See application file for complete search history.

(56) References Cited

U.S. PATENT DOCUMENTS

| | | |
|---|---|---|
| 371,664 A | 10/1887 | Brannan et al. |
| 702,472 A | 6/1902 | Pignolet |
| 728,883 A | 5/1903 | Downes |
| 1,586,645 A | 6/1926 | Bierman |
| 1,813,902 A | 7/1931 | Bovie |
| 1,822,330 A | 9/1931 | Ainslie |
| 1,852,542 A | 4/1932 | Sovatkin |
| 2,002,594 A | 5/1935 | Wappler et al. |
| 2,011,169 A | 8/1935 | Wappler |
| 2,031,682 A | 2/1936 | Wappler et al. |
| 2,054,149 A | 9/1936 | Wappler |
| 2,176,479 A | 10/1939 | Willis |
| 2,305,156 A | 4/1941 | Grubel |
| 2,279,753 A | 4/1942 | Knopp |
| 2,327,353 A | 8/1943 | Karle |
| 2,632,661 A | 8/1948 | Cristofv |
| 2,668,538 A | 2/1954 | Baker |
| 2,796,065 A | 6/1957 | Kapp |
| 3,073,311 A | 1/1963 | Tibbs et al. |
| 3,372,288 A | 3/1968 | Wigington |
| 3,459,187 A | 8/1969 | Pallotta |
| 3,643,663 A | 2/1972 | Sutter |
| 3,648,001 A | 3/1972 | Anderson et al. |
| 3,651,811 A | 3/1972 | Hildebrandt et al. |
| 3,678,229 A | 7/1972 | Osika |
| 3,720,896 A | 3/1973 | Beierlein |
| 3,763,726 A | 10/1973 | Hildebrand |
| 3,779,918 A | 12/1973 | Ikeda et al. |
| 3,801,766 A | 4/1974 | Morrison, Jr. |
| 3,862,630 A | 1/1975 | Balamuth |

(Continued)

FOREIGN PATENT DOCUMENTS

CA     2104423     2/1994

(Continued)

OTHER PUBLICATIONS

Michael Choti, "Abdominoperineal Resection with the LigaSure Vessel Sealing System and LigaSure Atlas 20 cm Open Instrument"; Innovations That Work, Jun. 2003.

(Continued)

*Primary Examiner* — Kevin C Sirmons
*Assistant Examiner* — Andrew Gilbert

(57) ABSTRACT

An electrosurgical instrument includes a support member and an electrode. The electrode is disposed on the support member and has a coating disposed thereon. The coating includes a seed layer and an atomic-layer-deposition ("ALD") layer. The ALD layer is hydrophobic or hydrophilic. The seed layer may be conductive or insulative.

5 Claims, 6 Drawing Sheets

U.S. PATENT DOCUMENTS

| | | |
|---|---|---|
| 3,863,339 A | 2/1975 | Reaney et al. |
| 3,866,610 A | 2/1975 | Kletschka |
| 3,911,766 A | 10/1975 | Fridolph et al. |
| 3,920,021 A | 11/1975 | Hiltebrandt |
| 3,921,641 A | 11/1975 | Hulka |
| 3,938,527 A | 2/1976 | Rioux et al. |
| 3,952,749 A | 4/1976 | Fridolph et al. |
| 3,970,088 A | 7/1976 | Morrison |
| 3,987,795 A | 10/1976 | Morrison |
| 4,005,714 A | 2/1977 | Hiltebrandt |
| 4,016,881 A | 4/1977 | Rioux et al. |
| 4,041,952 A | 8/1977 | Morrison, Jr. et al. |
| 4,043,342 A | 8/1977 | Morrison, Jr. |
| 4,074,718 A | 2/1978 | Morrison, Jr. |
| 4,076,028 A | 2/1978 | Simmons |
| 4,080,820 A | 3/1978 | Allen |
| 4,088,134 A | 5/1978 | Mazzariello |
| 4,112,950 A | 9/1978 | Pike |
| 4,127,222 A | 11/1978 | Adams |
| 4,128,099 A | 12/1978 | Bauer |
| 4,165,746 A | 8/1979 | Burgin |
| 4,187,420 A | 2/1980 | Piber |
| 4,196,734 A | 4/1980 | Harris |
| 4,233,734 A | 11/1980 | Bies |
| 4,236,470 A | 12/1980 | Stenson |
| 4,300,564 A | 11/1981 | Furihata |
| 4,311,145 A | 1/1982 | Esty et al. |
| D263,020 S | 2/1982 | Rau, III |
| 4,370,980 A | 2/1983 | Lottick |
| 4,375,218 A | 3/1983 | DiGeronimo |
| 4,416,276 A | 11/1983 | Newton et al. |
| 4,418,692 A | 12/1983 | Guay |
| 4,443,935 A | 4/1984 | Zamba et al. |
| 4,452,246 A | 6/1984 | Bader et al. |
| 4,470,786 A | 9/1984 | Sano et al. |
| 4,492,231 A | 1/1985 | Auth |
| 4,493,320 A | 1/1985 | Treat |
| 4,503,855 A | 3/1985 | Maslanka |
| 4,506,669 A | 3/1985 | Blake, III |
| 4,509,518 A | 4/1985 | McGarry et al. |
| 4,552,143 A | 11/1985 | Lottick |
| 4,574,804 A | 3/1986 | Kurwa |
| 4,597,379 A | 7/1986 | Kihn et al. |
| 4,600,007 A | 7/1986 | Lahodny et al. |
| 4,624,254 A | 11/1986 | McGarry et al. |
| 4,655,215 A | 4/1987 | Pike |
| 4,655,216 A | 4/1987 | Tischer |
| 4,657,016 A | 4/1987 | Garito et al. |
| 4,662,372 A | 5/1987 | Sharkany et al. |
| 4,671,274 A | 6/1987 | Sorochenko |
| 4,685,459 A | 8/1987 | Xoch et al. |
| 4,733,662 A | 3/1988 | DeSatnick et al. |
| D295,893 S | 5/1988 | Sharkany et al. |
| D295,894 S | 5/1988 | Sharkany et al. |
| 4,754,892 A | 7/1988 | Retief |
| 4,763,669 A | 8/1988 | Jaeger |
| 4,781,175 A * | 11/1988 | McGreevy et al. ............. 606/40 |
| 4,827,929 A | 5/1989 | Hodge |
| 4,829,313 A | 5/1989 | Taggart |
| 4,846,171 A | 7/1989 | Kauphusman et al. |
| 4,887,612 A | 12/1989 | Esser et al. |
| 4,938,761 A | 7/1990 | Ensslin |
| 4,947,009 A | 8/1990 | Osika et al. |
| 4,985,030 A | 1/1991 | Melzer et al. |
| 5,007,908 A | 4/1991 | Rydell |
| 5,026,370 A | 6/1991 | Lottick |
| 5,026,371 A | 6/1991 | Rydell et al. |
| 5,035,695 A | 7/1991 | Weber, Jr. et al. |
| 5,037,433 A | 8/1991 | Wilk et al. |
| 5,042,707 A | 8/1991 | Taheri |
| 5,047,046 A | 9/1991 | Bodoia |
| 5,078,716 A | 1/1992 | Doll |
| 5,084,057 A | 1/1992 | Green et al. |
| 5,085,659 A | 2/1992 | Rydell |
| 5,099,840 A | 3/1992 | Goble et al. |
| 5,100,430 A | 3/1992 | Avellanet et al. |
| 5,108,392 A | 4/1992 | Spingler |
| 5,112,343 A | 5/1992 | Thornton |
| 5,116,332 A | 5/1992 | Lottick |
| 5,147,357 A | 9/1992 | Rose et al. |
| 5,151,102 A | 9/1992 | Kamiyama et al. |
| 5,151,978 A | 9/1992 | Bronikowski et al. |
| 5,176,695 A | 1/1993 | Dulebohn |
| 5,190,541 A | 3/1993 | Abele et al. |
| 5,196,009 A | 3/1993 | Kirwan, Jr. |
| 5,197,964 A | 3/1993 | Parins |
| 5,209,747 A | 5/1993 | Knoepfler |
| 5,211,655 A | 5/1993 | Hasson |
| 5,215,101 A | 6/1993 | Jacobs et al. |
| 5,217,457 A | 6/1993 | Delahuerga et al. |
| 5,217,458 A | 6/1993 | Parins |
| 5,217,460 A | 6/1993 | Knoepfler |
| 5,219,354 A | 6/1993 | Choudhury et al. |
| 5,244,462 A | 9/1993 | Delahuerga et al. |
| 5,250,047 A | 10/1993 | Rydell |
| 5,250,063 A | 10/1993 | Abidin et al. |
| 5,258,001 A | 11/1993 | Corman |
| 5,258,006 A | 11/1993 | Rydell et al. |
| 5,261,918 A | 11/1993 | Phillips et al. |
| 5,275,615 A | 1/1994 | Rose |
| 5,277,201 A | 1/1994 | Stern |
| 5,282,799 A | 2/1994 | Rydell |
| 5,282,800 A | 2/1994 | Foshee et al. |
| 5,282,826 A | 2/1994 | Quadri |
| 5,290,286 A | 3/1994 | Parins |
| 5,300,082 A | 4/1994 | Sharpe et al. |
| 5,304,203 A | 4/1994 | El-Mallawany et al. |
| 5,308,353 A | 5/1994 | Beurrier |
| 5,308,357 A | 5/1994 | Lichtman |
| 5,313,027 A | 5/1994 | Inoue et al. |
| 5,314,445 A | 5/1994 | Degwitz et al. |
| 5,318,589 A | 6/1994 | Lichtman |
| 5,324,289 A | 6/1994 | Eggers |
| D348,930 S | 7/1994 | Olson |
| 5,326,806 A | 7/1994 | Yokoshima et al. |
| 5,330,471 A | 7/1994 | Eggers |
| 5,330,502 A | 7/1994 | Hassler et al. |
| 5,334,183 A | 8/1994 | Wuchinich |
| 5,334,215 A | 8/1994 | Chen |
| 5,336,220 A | 8/1994 | Ryan et al. |
| 5,336,221 A | 8/1994 | Anderson |
| 5,342,359 A | 8/1994 | Rydell |
| 5,342,381 A | 8/1994 | Tidemand |
| 5,342,393 A | 8/1994 | Stack |
| 5,344,424 A | 9/1994 | Roberts et al. |
| 5,350,391 A | 9/1994 | Iacovelli |
| 5,352,222 A | 10/1994 | Rydell |
| 5,354,271 A | 10/1994 | Voda |
| 5,356,408 A | 10/1994 | Rydell |
| 5,366,477 A | 11/1994 | LeMarie, III et al. |
| 5,368,600 A | 11/1994 | Failla et al. |
| 5,374,277 A | 12/1994 | Hassler |
| 5,376,089 A | 12/1994 | Smith |
| 5,383,875 A | 1/1995 | Bays et al. |
| 5,383,897 A | 1/1995 | Wholey |
| 5,389,098 A | 2/1995 | Tsuruta et al. |
| 5,389,103 A | 2/1995 | Melzer et al. |
| 5,389,104 A | 2/1995 | Hahnen et al. |
| 5,391,166 A | 2/1995 | Eggers |
| 5,391,183 A | 2/1995 | Janzen et al. |
| 5,396,900 A | 3/1995 | Slater et al. |
| 5,403,312 A | 4/1995 | Yates et al. |
| 5,403,342 A | 4/1995 | Tovey et al. |
| 5,405,344 A | 4/1995 | Williamson et al. |
| 5,409,763 A | 4/1995 | Serizawa et al. |
| 5,411,519 A | 5/1995 | Tovey et al. |
| 5,411,520 A | 5/1995 | Nash et al. |
| 5,413,571 A | 5/1995 | Katsaros et al. |
| 5,415,656 A | 5/1995 | Tihon et al. |
| 5,415,657 A | 5/1995 | Taymor-Luria |
| 5,422,567 A | 6/1995 | Matsunaga |
| 5,423,810 A | 6/1995 | Goble et al. |
| 5,425,690 A | 6/1995 | Chang |
| 5,425,739 A | 6/1995 | Jessen |
| 5,429,616 A | 7/1995 | Schaffer |
| 5,431,672 A | 7/1995 | Cote et al. |
| 5,431,674 A | 7/1995 | Basile et al. |

| Patent No. | Kind | Date | Inventor |
|---|---|---|---|
| 5,437,292 | A | 8/1995 | Kipshidze et al. |
| 5,438,302 | A | 8/1995 | Goble |
| 5,439,478 | A | 8/1995 | Palmer |
| 5,441,517 | A | 8/1995 | Kensey et al. |
| 5,443,463 | A | 8/1995 | Stern et al. |
| 5,443,464 | A | 8/1995 | Russell et al. |
| 5,443,480 | A | 8/1995 | Jacobs et al. |
| 5,445,638 | A | 8/1995 | Rydell et al. |
| 5,445,658 | A | 8/1995 | Durrfeld et al. |
| 5,449,480 | A | 9/1995 | Kuriya et al. |
| 5,451,224 | A | 9/1995 | Goble et al. |
| 5,454,823 | A | 10/1995 | Richardson et al. |
| 5,454,827 | A | 10/1995 | Aust et al. |
| 5,456,684 | A | 10/1995 | Schmidt et al. |
| 5,458,598 | A | 10/1995 | Feinberg et al. |
| 5,460,629 | A | 10/1995 | Shlain et al. |
| 5,461,765 | A | 10/1995 | Linden et al. |
| 5,462,546 | A | 10/1995 | Rydell |
| 5,472,442 | A | 12/1995 | Klicek |
| 5,472,443 | A | 12/1995 | Cordis et al. |
| 5,478,351 | A | 12/1995 | Meade et al. |
| 5,480,406 | A | 1/1996 | Nolan et al. |
| 5,480,409 | A | 1/1996 | Riza |
| 5,484,436 | A | 1/1996 | Eggers et al. |
| 5,496,312 | A | 3/1996 | Klicek |
| 5,496,317 | A | 3/1996 | Goble et al. |
| 5,496,347 | A | 3/1996 | Hashiguchi et al. |
| 5,499,997 | A | 3/1996 | Sharpe et al. |
| 5,509,922 | A | 4/1996 | Aranyi et al. |
| 5,512,721 | A | 4/1996 | Young et al. |
| 5,514,134 | A | 5/1996 | Rydell et al. |
| 5,527,313 | A | 6/1996 | Scott et al. |
| 5,528,833 | A | 6/1996 | Sakuma |
| 5,529,067 | A | 6/1996 | Larsen et al. |
| 5,531,744 | A | 7/1996 | Nardella et al. |
| 5,536,251 | A | 7/1996 | Evard et al. |
| 5,540,684 | A | 7/1996 | Hassler, Jr. |
| 5,540,685 | A | 7/1996 | Parins et al. |
| 5,540,706 | A | 7/1996 | Aust et al. |
| 5,540,715 | A | 7/1996 | Katsaros et al. |
| 5,542,945 | A | 8/1996 | Fritzsch |
| 5,558,671 | A | 9/1996 | Yates |
| 5,558,672 | A | 9/1996 | Edwards et al. |
| 5,562,619 | A | 10/1996 | Mirarchi et al. |
| 5,562,699 | A | 10/1996 | Heimberger et al. |
| 5,562,720 | A | 10/1996 | Stern et al. |
| 5,564,615 | A | 10/1996 | Bishop et al. |
| 5,569,241 | A | 10/1996 | Edwardds |
| 5,569,243 | A | 10/1996 | Kortenbach et al. |
| 5,571,100 | A | 11/1996 | Goble et al. |
| 5,573,424 | A | 11/1996 | Poppe |
| 5,573,534 | A | 11/1996 | Stone |
| 5,573,535 | A | 11/1996 | Viklund |
| 5,575,799 | A | 11/1996 | Bolanos et al. |
| 5,575,805 | A | 11/1996 | Li |
| 5,578,052 | A | 11/1996 | Koros et al. |
| 5,579,781 | A | 12/1996 | Cooke |
| 5,582,611 | A | 12/1996 | Tsukagoshi et al. |
| 5,582,617 | A | 12/1996 | Klieman et al. |
| 5,585,896 | A | 12/1996 | Yamazaki et al. |
| 5,590,570 | A | 1/1997 | LeMaire, III et al. |
| 5,591,181 | A | 1/1997 | Stone et al. |
| 5,597,107 | A | 1/1997 | Knodel et al. |
| 5,601,224 | A | 2/1997 | Bishop et al. |
| 5,601,601 | A | 2/1997 | Tal et al. |
| 5,601,641 | A | 2/1997 | Stephens |
| 5,603,711 | A | 2/1997 | Parins et al. |
| 5,603,723 | A | 2/1997 | Aranyi et al. |
| 5,611,798 | A | 3/1997 | Eggers |
| 5,611,808 | A | 3/1997 | Hossain et al. |
| 5,611,813 | A | 3/1997 | Lichtman |
| 5,620,415 | A | 4/1997 | Lucey et al. |
| 5,620,453 | A | 4/1997 | Nallakrishnan |
| 5,620,459 | A | 4/1997 | Lichtman |
| 5,624,452 | A | 4/1997 | Yates |
| 5,626,578 | A | 5/1997 | Tihon |
| 5,626,609 | A | 5/1997 | Zvenyatsky et al. |
| 5,630,833 | A | 5/1997 | Katsaros et al. |
| 5,637,110 | A | 6/1997 | Pennybacker et al. |
| 5,638,003 | A | 6/1997 | Hall |
| 5,643,294 | A | 7/1997 | Tovey et al. |
| 5,647,869 | A | 7/1997 | Goble et al. |
| 5,647,871 | A | 7/1997 | Levine et al. |
| 5,649,959 | A | 7/1997 | Hannam et al. |
| 5,655,650 | A | 8/1997 | Naitou |
| 5,658,281 | A | 8/1997 | Heard |
| D384,413 | S | 9/1997 | Zlock et al. |
| 5,662,667 | A | 9/1997 | Knodel |
| 5,665,100 | A | 9/1997 | Yoon |
| 5,667,526 | A | 9/1997 | Levin |
| 5,674,220 | A | 10/1997 | Fox et al. |
| 5,674,229 | A | 10/1997 | Tovey et al. |
| 5,681,282 | A | 10/1997 | Eggers et al. |
| 5,688,270 | A | 11/1997 | Yates et al. |
| 5,690,652 | A | 11/1997 | Wurster et al. |
| 5,690,653 | A | 11/1997 | Richardson et al. |
| 5,693,051 | A | 12/1997 | Schulze et al. |
| 5,693,920 | A | 12/1997 | Maeda |
| 5,695,522 | A | 12/1997 | LeMaire, III et al. |
| 5,700,261 | A | 12/1997 | Brinkerhoff |
| 5,700,270 | A | 12/1997 | Peyser et al. |
| 5,702,387 | A | 12/1997 | Arts et al. |
| 5,702,390 | A | 12/1997 | Austin et al. |
| 5,707,369 | A | 1/1998 | Vaitekunas et al. |
| 5,709,680 | A | 1/1998 | Yates et al. |
| 5,713,895 | A | 2/1998 | Lontine et al. |
| 5,716,366 | A | 2/1998 | Yates |
| 5,720,744 | A | 2/1998 | Eggleston et al. |
| 5,722,421 | A | 3/1998 | Francese et al. |
| 5,725,536 | A | 3/1998 | Oberlin et al. |
| 5,727,428 | A | 3/1998 | LeMaire, III et al. |
| 5,735,848 | A | 4/1998 | Yates et al. |
| 5,743,906 | A | 4/1998 | Parins et al. |
| 5,752,973 | A | 5/1998 | Kieturakis |
| 5,755,717 | A | 5/1998 | Yates et al. |
| 5,759,188 | A | 6/1998 | Yoon |
| 5,766,130 | A | 6/1998 | Selmonosky |
| 5,766,166 | A | 6/1998 | Hooven |
| 5,766,170 | A | 6/1998 | Eggers |
| 5,766,196 | A | 6/1998 | Griffiths |
| 5,769,849 | A | 6/1998 | Eggers |
| 5,772,655 | A | 6/1998 | Bauer et al. |
| 5,772,670 | A | 6/1998 | Brosa |
| 5,776,128 | A | 7/1998 | Eggers |
| 5,776,130 | A | 7/1998 | Buysse et al. |
| 5,779,646 | A | 7/1998 | Koblish et al. |
| 5,779,701 | A * | 7/1998 | McBrayer et al. .............. 606/46 |
| H1745 | H | 8/1998 | Paraschac |
| 5,792,137 | A | 8/1998 | Carr et al. |
| 5,792,165 | A | 8/1998 | Klieman et al. |
| 5,792,177 | A | 8/1998 | Kaseda |
| 5,797,537 | A | 8/1998 | Oberlin et al. |
| 5,797,927 | A | 8/1998 | Yoon |
| 5,797,938 | A | 8/1998 | Paraschac et al. |
| 5,797,941 | A | 8/1998 | Schulze et al. |
| 5,797,958 | A | 8/1998 | Yoon |
| 5,800,449 | A | 9/1998 | Wales |
| 5,807,393 | A | 9/1998 | Williamson, IV et al. |
| 5,810,764 | A | 9/1998 | Eggers et al. |
| 5,810,805 | A | 9/1998 | Sutcu et al. |
| 5,810,808 | A | 9/1998 | Eggers |
| 5,810,811 | A | 9/1998 | Yates et al. |
| 5,810,877 | A | 9/1998 | Roth et al. |
| 5,814,043 | A | 9/1998 | Shapeton |
| 5,814,054 | A | 9/1998 | Kortenbach et al. |
| 5,817,093 | A | 10/1998 | Williamson, IV et al. |
| 5,817,119 | A | 10/1998 | Klieman et al. |
| 5,820,630 | A | 10/1998 | Lind |
| 5,824,978 | A | 10/1998 | Karasik et al. |
| 5,827,271 | A | 10/1998 | Buysse et al. |
| 5,827,279 | A | 10/1998 | Hughett et al. |
| 5,827,281 | A | 10/1998 | Levin |
| 5,827,323 | A | 10/1998 | Klieman et al. |
| 5,827,548 | A | 10/1998 | Lavallee et al. |
| 5,833,690 | A | 11/1998 | Yates et al. |
| 5,843,080 | A | 12/1998 | Fleenor et al. |
| 5,849,022 | A | 12/1998 | Sakashita et al. |
| 5,853,412 | A | 12/1998 | Mayenberger |

| Patent | Date | Name |
|---|---|---|
| 5,859,527 A | 1/1999 | Cook |
| 5,860,976 A | 1/1999 | Billings et al. |
| 5,876,401 A | 3/1999 | Schulze et al. |
| 5,876,412 A | 3/1999 | Piraka |
| 5,882,567 A | 3/1999 | Cavallaro et al. |
| 5,891,141 A | 4/1999 | Rydell |
| 5,891,142 A | 4/1999 | Eggers et al. |
| 5,893,863 A | 4/1999 | Yoon |
| 5,893,875 A | 4/1999 | O'Connor et al. |
| 5,893,877 A | 4/1999 | Gampp, Jr. et al. |
| 5,897,563 A | 4/1999 | Yoon et al. |
| 5,902,301 A | 5/1999 | Olig |
| 5,906,630 A | 5/1999 | Anderhub et al. |
| 5,908,420 A | 6/1999 | Parins et al. |
| 5,908,432 A | 6/1999 | Pan |
| 5,911,719 A | 6/1999 | Eggers |
| 5,913,874 A | 6/1999 | Berns et al. |
| 5,921,916 A | 7/1999 | Aeikens et al. |
| 5,921,984 A | 7/1999 | Sutcu et al. |
| 5,925,043 A * | 7/1999 | Kumar et al. .................. 606/45 |
| 5,928,136 A | 7/1999 | Barry |
| 5,935,126 A | 8/1999 | Riza |
| 5,941,869 A | 8/1999 | Patterson et al. |
| 5,944,718 A | 8/1999 | Dafforn et al. |
| 5,951,546 A | 9/1999 | Lorentzen |
| 5,951,549 A | 9/1999 | Richardson et al. |
| 5,954,720 A | 9/1999 | Wilson et al. |
| 5,954,731 A | 9/1999 | Yoon |
| 5,954,733 A | 9/1999 | Yoon |
| 5,957,923 A | 9/1999 | Hahnen et al. |
| 5,957,937 A | 9/1999 | Yoon |
| 5,960,544 A | 10/1999 | Beyers |
| 5,961,514 A | 10/1999 | Long et al. |
| 5,964,758 A | 10/1999 | Dresden |
| 5,976,132 A | 11/1999 | Morris |
| 5,984,932 A | 11/1999 | Yoon |
| 5,984,938 A | 11/1999 | Yoon |
| 5,984,939 A | 11/1999 | Yoon |
| 5,989,277 A | 11/1999 | LeMaire, III et al. |
| 5,993,466 A | 11/1999 | Yoon |
| 5,993,467 A | 11/1999 | Yoon |
| 5,997,565 A | 12/1999 | Inoue |
| 6,004,332 A | 12/1999 | Yoon et al. |
| 6,004,335 A | 12/1999 | Vaitekunas et al. |
| 6,010,516 A | 1/2000 | Hulka et al. |
| 6,017,358 A | 1/2000 | Yoon et al. |
| 6,021,693 A | 2/2000 | Feng-Sing |
| 6,024,741 A | 2/2000 | Williamson et al. |
| 6,024,743 A | 2/2000 | Edwards |
| 6,024,744 A | 2/2000 | Kese et al. |
| 6,027,522 A | 2/2000 | Palmer |
| 6,030,384 A | 2/2000 | Nezhat |
| 6,033,399 A | 3/2000 | Gines |
| 6,039,733 A | 3/2000 | Buysse et al. |
| 6,041,679 A | 3/2000 | Slater et al. |
| 6,050,996 A | 4/2000 | Schmaltz et al. |
| 6,053,914 A | 4/2000 | Eggers et al. |
| 6,053,933 A | 4/2000 | Balazs et al. |
| D424,694 S | 5/2000 | Tetzlaff et al. |
| D425,201 S | 5/2000 | Tetzlaff et al. |
| 6,059,782 A | 5/2000 | Novak et al. |
| 6,066,139 A | 5/2000 | Ryan et al. |
| 6,070,444 A | 6/2000 | Lontine et al. |
| 6,071,283 A | 6/2000 | Nardella et al. |
| 6,074,386 A | 6/2000 | Goble et al. |
| 6,077,287 A | 6/2000 | Taylor et al. |
| 6,080,152 A | 6/2000 | Nardella et al. |
| 6,080,180 A | 6/2000 | Yoon et al. |
| RE36,795 E | 7/2000 | Rydell |
| 6,083,223 A | 7/2000 | Baker |
| 6,086,586 A | 7/2000 | Hooven |
| 6,086,601 A | 7/2000 | Yoon |
| 6,090,107 A | 7/2000 | Borgmeier et al. |
| 6,096,037 A | 8/2000 | Mulier et al. |
| 6,099,550 A | 8/2000 | Yoon |
| 6,102,909 A | 8/2000 | Chen et al. |
| 6,106,542 A | 8/2000 | Toybin et al. |
| 6,110,171 A | 8/2000 | Rydell |
| 6,113,596 A | 9/2000 | Hooven et al. |
| 6,113,598 A | 9/2000 | Baker |
| 6,117,158 A | 9/2000 | Measamer et al. |
| 6,122,549 A | 9/2000 | Sharkey et al. |
| 6,123,701 A | 9/2000 | Nezhat |
| H1904 H | 10/2000 | Yates et al. |
| 6,126,658 A | 10/2000 | Baker |
| 6,126,665 A | 10/2000 | Yoon |
| 6,139,547 A | 10/2000 | Lontine et al. |
| 6,139,563 A | 10/2000 | Cosgrove, III et al. |
| 6,143,005 A | 11/2000 | Yoon et al. |
| 6,152,923 A | 11/2000 | Ryan |
| 6,162,220 A | 12/2000 | Nezhat |
| 6,171,316 B1 | 1/2001 | Kovac et al. |
| 6,174,309 B1 | 1/2001 | Wrublewski et al. |
| 6,178,628 B1 | 1/2001 | Clemens et al. |
| 6,179,834 B1 | 1/2001 | Buysse et al. |
| 6,179,837 B1 | 1/2001 | Hooven |
| 6,183,467 B1 | 2/2001 | Shapeton et al. |
| 6,187,003 B1 | 2/2001 | Buysse et al. |
| 6,190,386 B1 | 2/2001 | Rydell |
| 6,190,400 B1 | 2/2001 | Vandemoer et al. |
| 6,193,718 B1 | 2/2001 | Kortenbach et al. |
| 6,206,876 B1 | 3/2001 | Levine et al. |
| 6,206,877 B1 | 3/2001 | Kese et al. |
| 6,206,893 B1 | 3/2001 | Klein et al. |
| 6,214,028 B1 | 4/2001 | Yoon et al. |
| 6,217,602 B1 | 4/2001 | Redmon |
| 6,217,615 B1 | 4/2001 | Sioshansi et al. |
| 6,221,039 B1 | 4/2001 | Durgin et al. |
| 6,223,100 B1 | 4/2001 | Green |
| 6,224,593 B1 | 5/2001 | Ryan et al. |
| 6,224,614 B1 | 5/2001 | Yoon |
| 6,228,080 B1 | 5/2001 | Gines |
| 6,228,083 B1 | 5/2001 | Lands et al. |
| 6,248,124 B1 | 6/2001 | Pedros et al. |
| 6,248,944 B1 | 6/2001 | Ito |
| 6,261,307 B1 | 7/2001 | Yoon et al. |
| 6,267,758 B1 * | 7/2001 | Daw et al. .................. 606/42 |
| 6,267,761 B1 | 7/2001 | Ryan |
| 6,270,497 B1 | 8/2001 | Sekino et al. |
| 6,270,508 B1 | 8/2001 | Klieman et al. |
| 6,273,887 B1 | 8/2001 | Yamauchi et al. |
| 6,277,117 B1 | 8/2001 | Tetzlaff et al. |
| 6,280,458 B1 | 8/2001 | Boche et al. |
| 6,283,961 B1 | 9/2001 | Underwood et al. |
| D449,886 S | 10/2001 | Tetzlaff et al. |
| 6,298,550 B1 | 10/2001 | Kirwan |
| 6,302,424 B1 | 10/2001 | Gisinger et al. |
| 6,319,262 B1 | 11/2001 | Bates et al. |
| 6,319,451 B1 | 11/2001 | Brune |
| 6,322,561 B1 | 11/2001 | Eggers et al. |
| 6,322,580 B1 | 11/2001 | Kanner |
| 6,325,795 B1 | 12/2001 | Lindemann et al. |
| 6,334,860 B1 | 1/2002 | Dorn |
| 6,334,861 B1 | 1/2002 | Chandler et al. |
| 6,345,532 B1 | 2/2002 | Coudray et al. |
| 6,350,264 B1 | 2/2002 | Hooven |
| 6,352,536 B1 | 3/2002 | Buysse et al. |
| 6,358,249 B1 | 3/2002 | Chen et al. |
| 6,358,259 B1 | 3/2002 | Swain et al. |
| 6,358,268 B1 | 3/2002 | Hunt et al. |
| 6,364,879 B1 | 4/2002 | Chen et al. |
| D457,958 S | 5/2002 | Dycus et al. |
| D457,959 S | 5/2002 | Tetzlaff et al. |
| 6,387,094 B1 | 5/2002 | Eitenmuller |
| 6,391,035 B1 | 5/2002 | Appleby et al. |
| 6,398,779 B1 | 6/2002 | Buysse et al. |
| 6,402,747 B1 | 6/2002 | Lindemann et al. |
| 6,409,728 B1 | 6/2002 | Ehr et al. |
| H2037 H | 7/2002 | Yates et al. |
| 6,413,255 B1 | 7/2002 | Stern |
| 6,419,675 B1 | 7/2002 | Gallo, Sr. |
| 6,425,896 B1 | 7/2002 | Baltschun et al. |
| 6,432,112 B2 | 8/2002 | Brock et al. |
| 6,440,144 B1 | 8/2002 | Bacher |
| 6,443,952 B1 | 9/2002 | Mulier et al. |
| 6,443,970 B1 | 9/2002 | Schulze et al. |
| 6,451,018 B1 | 9/2002 | Lands et al. |
| 6,458,125 B1 | 10/2002 | Cosmescu |

| | | | | | | |
|---|---|---|---|---|---|---|
| 6,458,128 B1 | 10/2002 | Schulze | | 6,776,780 B2 | 8/2004 | Mulier et al. |
| 6,458,130 B1 | 10/2002 | Frazier et al. | | 6,786,905 B2 | 9/2004 | Swanson et al. |
| 6,461,352 B2 | 10/2002 | Morgan et al. | | 6,790,217 B2 | 9/2004 | Schulze et al. |
| 6,461,368 B2 | 10/2002 | Fogarty et al. | | 6,796,981 B2 | 9/2004 | Wham et al. |
| 6,464,701 B1 | 10/2002 | Hooven et al. | | D496,997 S | 10/2004 | Dycus et al. |
| 6,464,702 B2 | 10/2002 | Schulze et al. | | 6,800,825 B1 | 10/2004 | Sasaki et al. |
| 6,464,704 B2 | 10/2002 | Schmaltz et al. | | 6,802,843 B2 | 10/2004 | Truckai et al. |
| 6,472,062 B1 | 10/2002 | Neerinck et al. | | 6,808,525 B2 | 10/2004 | Latterell et al. |
| 6,485,489 B2 | 11/2002 | Teirstein et al. | | D499,181 S | 11/2004 | Dycus et al. |
| 6,494,888 B1 | 12/2002 | Laufer et al. | | 6,818,000 B2 | 11/2004 | Muller et al. |
| 6,500,176 B1 | 12/2002 | Truckai et al. | | 6,821,285 B2 | 11/2004 | Laufer et al. |
| 6,506,196 B1 | 1/2003 | Laufer | | 6,835,200 B2 | 12/2004 | Laufer et al. |
| 6,508,815 B1 | 1/2003 | Strul et al. | | 6,857,357 B2 | 2/2005 | Fujii |
| 6,511,480 B1 | 1/2003 | Tetzlaff et al. | | 6,860,880 B2 | 3/2005 | Treat et al. |
| 6,514,215 B1 | 2/2003 | Ouchi | | 6,887,240 B1 | 5/2005 | Lands et al. |
| 6,514,252 B2 | 2/2003 | Nezhat et al. | | 6,889,116 B2 | 5/2005 | Jinno |
| 6,517,539 B1 | 2/2003 | Smith et al. | | 6,914,201 B2 | 7/2005 | Van Vooren et al. |
| 6,527,771 B1 | 3/2003 | Weadock et al. | | 6,926,716 B2 | 8/2005 | Baker et al. |
| 6,533,784 B2 | 3/2003 | Truckai et al. | | 6,929,644 B2 | 8/2005 | Truckai et al. |
| 6,540,745 B1 * | 4/2003 | Fairbourn et al. ............ 606/45 | | 6,932,810 B2 | 8/2005 | Ryan |
| 6,545,239 B2 | 4/2003 | Spedale et al. | | 6,932,816 B2 | 8/2005 | Phan |
| 6,558,385 B1 | 5/2003 | McClurken et al. | | 6,934,134 B2 | 8/2005 | Mori et al. |
| 6,562,037 B2 | 5/2003 | Paton et al. | | 6,936,061 B2 | 8/2005 | Sasaki |
| 6,569,105 B1 | 5/2003 | Kortenbach et al. | | D509,297 S | 9/2005 | Wells |
| 6,582,427 B1 | 6/2003 | Goble et al. | | 6,942,662 B2 | 9/2005 | Goble et al. |
| 6,582,450 B2 | 6/2003 | Ouchi | | 6,943,311 B2 | 9/2005 | Miyako |
| 6,585,735 B1 | 7/2003 | Frazier et al. | | 6,951,559 B1 | 10/2005 | Greep |
| 6,602,252 B2 | 8/2003 | Mollenauer | | 6,953,430 B2 | 10/2005 | Kodooka |
| 6,605,790 B2 | 8/2003 | Yoshida | | 6,953,461 B2 | 10/2005 | McClurken et al. |
| 6,613,432 B2 | 9/2003 | Zamora et al. | | 6,958,070 B2 | 10/2005 | Witt et al. |
| 6,616,658 B2 | 9/2003 | Ineson | | 6,960,210 B2 | 11/2005 | Lands et al. |
| 6,616,661 B2 | 9/2003 | Wellman et al. | | 6,964,662 B2 | 11/2005 | Kidooka |
| 6,620,161 B2 | 9/2003 | Schulze et al. | | 6,966,907 B2 | 11/2005 | Goble |
| 6,620,184 B2 | 9/2003 | De Laforcade et al. | | 6,972,017 B2 | 12/2005 | Smith et al. |
| 6,626,901 B1 | 9/2003 | Treat et al. | | 6,974,452 B1 * | 12/2005 | Gille et al. ............ 606/37 |
| 6,638,287 B2 | 10/2003 | Danitz et al. | | 6,977,495 B2 | 12/2005 | Donofrio |
| 6,641,595 B1 | 11/2003 | Moran et al. | | 6,979,786 B2 | 12/2005 | Aukland et al. |
| 6,652,514 B2 | 11/2003 | Ellman et al. | | 6,981,628 B2 | 1/2006 | Wales |
| 6,652,521 B2 | 11/2003 | Schulze | | 6,987,244 B2 | 1/2006 | Bauer |
| 6,656,175 B2 | 12/2003 | Francischelli et al. | | 6,994,707 B2 | 2/2006 | Ellman et al. |
| 6,656,177 B2 | 12/2003 | Truckai et al. | | 6,994,709 B2 | 2/2006 | Iida |
| 6,660,072 B2 | 12/2003 | Chatterjee | | 6,997,931 B2 | 2/2006 | Sauer et al. |
| 6,663,639 B1 | 12/2003 | Laufer et al. | | 7,001,381 B2 | 2/2006 | Harano et al. |
| 6,663,641 B1 | 12/2003 | Kovac et al. | | 7,011,657 B2 | 3/2006 | Truckai et al. |
| 6,666,854 B1 | 12/2003 | Lange | | 7,033,354 B2 | 4/2006 | Keppel |
| 6,669,696 B2 | 12/2003 | Bacher et al. | | 7,033,356 B2 | 4/2006 | Latterell et al. |
| 6,673,092 B1 | 1/2004 | Bacher | | 7,041,102 B2 | 5/2006 | Truckai et al. |
| 6,676,660 B2 | 1/2004 | Wampler et al. | | 7,044,948 B2 | 5/2006 | Keppel |
| 6,676,676 B2 | 1/2004 | Danitz et al. | | 7,052,489 B2 | 5/2006 | Griego et al. |
| 6,679,882 B1 | 1/2004 | Kornerup | | 7,052,496 B2 | 5/2006 | Yamauchi |
| 6,682,527 B2 | 1/2004 | Strul | | 7,063,715 B2 | 6/2006 | Onuki et al. |
| 6,682,528 B2 | 1/2004 | Frazier et al. | | D525,361 S | 7/2006 | Hushka |
| 6,685,724 B1 | 2/2004 | Haluck | | 7,070,597 B2 | 7/2006 | Truckai et al. |
| 6,689,131 B2 | 2/2004 | McClurken | | 7,083,618 B2 | 8/2006 | Couture et al. |
| 6,692,445 B2 | 2/2004 | Roberts et al. | | 7,083,619 B2 | 8/2006 | Truckai et al. |
| 6,693,246 B1 | 2/2004 | Rudolph et al. | | 7,083,620 B2 | 8/2006 | Jahns et al. |
| 6,695,840 B2 | 2/2004 | Schulze | | 7,087,051 B2 | 8/2006 | Bourne et al. |
| 6,702,810 B2 | 3/2004 | McClurken et al. | | 7,087,054 B2 | 8/2006 | Truckai et al. |
| 6,723,092 B2 | 4/2004 | Brown et al. | | 7,090,673 B2 | 8/2006 | Dycus et al. |
| 6,726,068 B2 | 4/2004 | Miller | | 7,090,689 B2 | 8/2006 | Nagase et al. |
| 6,726,686 B2 | 4/2004 | Buysse et al. | | 7,101,371 B2 | 9/2006 | Dycus et al. |
| 6,726,694 B2 | 4/2004 | Blatter et al. | | 7,101,372 B2 | 9/2006 | Dycus et al. |
| 6,733,498 B2 | 5/2004 | Paton et al. | | 7,101,373 B2 | 9/2006 | Dycus et al. |
| 6,736,813 B2 | 5/2004 | Yamauchi et al. | | 7,103,947 B2 | 9/2006 | Sartor et al. |
| 6,743,229 B2 | 6/2004 | Buysse et al. | | 7,107,124 B2 | 9/2006 | Green |
| 6,743,230 B2 | 6/2004 | Lutze et al. | | 7,112,199 B2 | 9/2006 | Cosmescu |
| 6,743,239 B1 | 6/2004 | Kuehn et al. | | D531,311 S | 10/2006 | Guerra et al. |
| 6,743,240 B2 | 6/2004 | Smith et al. | | 7,115,123 B2 | 10/2006 | Knowlton et al. |
| 6,755,843 B2 | 6/2004 | Chung et al. | | 7,118,570 B2 | 10/2006 | Tetzlaff et al. |
| 6,756,553 B1 | 6/2004 | Yamaguchi et al. | | 7,118,587 B2 | 10/2006 | Dycus et al. |
| 6,757,977 B2 | 7/2004 | Dambal et al. | | 7,131,860 B2 | 11/2006 | Sartor et al. |
| 6,758,846 B2 | 7/2004 | Goble et al. | | 7,131,970 B2 | 11/2006 | Moses et al. |
| D493,888 S | 8/2004 | Reschke | | 7,131,971 B2 | 11/2006 | Dycus et al. |
| 6,770,072 B1 * | 8/2004 | Truckai et al. ............ 606/52 | | 7,135,020 B2 | 11/2006 | Lawes et al. |
| 6,773,409 B2 | 8/2004 | Truckai et al. | | D533,942 S | 12/2006 | Kerr et al. |
| 6,773,432 B1 | 8/2004 | Clayman et al. | | 7,145,757 B2 | 12/2006 | Shea et al. |
| 6,773,434 B2 | 8/2004 | Ciarrocca | | 7,147,634 B2 | 12/2006 | Nesbitt |
| 6,773,441 B1 | 8/2004 | Laufer et al. | | 7,147,638 B2 | 12/2006 | Chapman et al. |
| 6,775,575 B2 | 8/2004 | Bommannan et al. | | 7,150,097 B2 | 12/2006 | Sremcich et al. |

| | | | | | | |
|---|---|---|---|---|---|---|
| 7,150,749 B2 | 12/2006 | Dycus et al. | | 2003/0014052 A1 | 1/2003 | Buysse et al. |
| 7,153,314 B2 | 12/2006 | Laufer et al. | | 2003/0014053 A1 | 1/2003 | Nguyen et al. |
| D535,027 S | 1/2007 | James et al. | | 2003/0018331 A1 | 1/2003 | Dycus et al. |
| 7,156,842 B2 | 1/2007 | Sartor et al. | | 2003/0018332 A1 | 1/2003 | Schmaltz et al. |
| 7,156,846 B2 | 1/2007 | Dycus et al. | | 2003/0032956 A1 | 2/2003 | Lands et al. |
| 7,160,297 B2 | 1/2007 | Nesbitt | | 2003/0069570 A1 | 4/2003 | Witzel et al. |
| 7,160,298 B2 | 1/2007 | Lawes et al. | | 2003/0069571 A1 | 4/2003 | Treat et al. |
| 7,160,299 B2 | 1/2007 | Baily | | 2003/0078578 A1 | 4/2003 | Truckai et al. |
| 7,169,146 B2 | 1/2007 | Truckai et al. | | 2003/0109875 A1 | 6/2003 | Tetzlaff et al. |
| 7,179,255 B2 | 2/2007 | Lettice et al. | | 2003/0114851 A1 | 6/2003 | Truckai et al. |
| 7,179,258 B2 | 2/2007 | Buysse et al. | | 2003/0139741 A1 | 7/2003 | Goble et al. |
| 7,195,631 B2 | 3/2007 | Dumbauld | | 2003/0139742 A1 | 7/2003 | Wampler et al. |
| D541,418 S | 4/2007 | Schechter et al. | | 2003/0153908 A1 | 8/2003 | Goble et al. |
| 7,207,990 B2 | 4/2007 | Lands et al. | | 2003/0158548 A1 | 8/2003 | Phan et al. |
| D541,938 S | 5/2007 | Kerr et al. | | 2003/0158549 A1 | 8/2003 | Swanson |
| 7,223,264 B2 | 5/2007 | Daniel et al. | | 2003/0163125 A1* | 8/2003 | Greep ............................ 606/41 |
| 7,223,265 B2 | 5/2007 | Keppel | | 2003/0171747 A1 | 9/2003 | Kanehira et al. |
| 7,232,440 B2 | 6/2007 | Dumbauld et al. | | 2003/0181910 A1 | 9/2003 | Dycus et al. |
| 7,241,288 B2 | 7/2007 | Braun | | 2003/0216732 A1 | 11/2003 | Truckai et al. |
| 7,241,296 B2 | 7/2007 | Buysse et al. | | 2003/0220637 A1 | 11/2003 | Truckai et al. |
| 7,244,257 B2 | 7/2007 | Podjahsky et al. | | 2003/0229344 A1 | 12/2003 | Dycus et al. |
| 7,246,734 B2 | 7/2007 | Shelto, IV | | 2003/0236325 A1 | 12/2003 | Bonora |
| 7,248,944 B2 | 7/2007 | Green | | 2003/0236518 A1 | 12/2003 | Marchitto et al. |
| 7,252,667 B2 | 8/2007 | Moses et al. | | 2004/0030330 A1 | 2/2004 | Brassell et al. |
| 7,255,697 B2 | 8/2007 | Dycus et al. | | 2004/0030332 A1 | 2/2004 | Knowlton et al. |
| 7,267,677 B2 | 9/2007 | Johnson et al. | | 2004/0049185 A1 | 3/2004 | Latterell et al. |
| 7,270,660 B2 | 9/2007 | Ryan | | 2004/0064151 A1 | 4/2004 | Mollenauer |
| 7,270,664 B2 | 9/2007 | Johnson et al. | | 2004/0073238 A1 | 4/2004 | Makower |
| 7,276,068 B2 | 10/2007 | Johnson et al. | | 2004/0073256 A1 | 4/2004 | Marchitto et al. |
| 7,288,091 B2 | 10/2007 | Nesbitt | | 2004/0078035 A1 | 4/2004 | Kanehira et al. |
| 7,300,435 B2 | 11/2007 | Wham et al. | | 2004/0082952 A1 | 4/2004 | Dycus et al. |
| 7,303,557 B2 | 12/2007 | Wham et al. | | 2004/0087943 A1 | 5/2004 | Dycus et al. |
| 7,311,709 B2 | 12/2007 | Truckai et al. | | 2004/0115296 A1 | 6/2004 | Duffin |
| 7,314,471 B2 | 1/2008 | Holman | | 2004/0116792 A1 | 6/2004 | Nesbitt |
| 7,318,823 B2 | 1/2008 | Sharps et al. | | 2004/0116924 A1 | 6/2004 | Dycus et al. |
| 7,329,256 B2 | 2/2008 | Johnson et al. | | 2004/0116979 A1 | 6/2004 | Truckai et al. |
| 7,329,257 B2 | 2/2008 | Kanehira et al. | | 2004/0126596 A1 | 7/2004 | Zamora et al. |
| D564,662 S | 3/2008 | Moses et al. | | 2004/0143263 A1 | 7/2004 | Schechter et al. |
| 7,338,526 B2 | 3/2008 | Steinberg | | 2004/0148035 A1 | 7/2004 | Barrett et al. |
| 7,342,754 B2 | 3/2008 | Fitzgerald et al. | | 2004/0162557 A1 | 8/2004 | Tetzlaff et al. |
| 7,344,268 B2 | 3/2008 | Jhigamian | | 2004/0181219 A1 | 9/2004 | Goble et al. |
| D567,943 S | 4/2008 | Moses et al. | | 2004/0193153 A1 | 9/2004 | Sartor et al. |
| 7,367,976 B2 | 5/2008 | Lawes et al. | | 2004/0199181 A1 | 10/2004 | Knodel et al. |
| 7,377,920 B2 | 5/2008 | Buysse et al. | | 2004/0210282 A1 | 10/2004 | Flock et al. |
| 7,384,420 B2 | 6/2008 | Dycus et al. | | 2004/0224590 A1 | 11/2004 | Rawa et al. |
| 7,384,421 B2 | 6/2008 | Hushka | | 2004/0230189 A1 | 11/2004 | Keppel |
| 7,390,326 B2 | 6/2008 | Nesbitt | | 2004/0236326 A1 | 11/2004 | Schulze et al. |
| 7,396,336 B2 | 7/2008 | Orszulak et al. | | 2004/0243125 A1 | 12/2004 | Dycus et al. |
| D575,395 S | 8/2008 | Hushka | | 2004/0249374 A1 | 12/2004 | Tetzlaff et al. |
| D575,401 S | 8/2008 | Hixson et al. | | 2004/0260281 A1 | 12/2004 | Baxter, III et al. |
| 7,435,249 B2 | 10/2008 | Buysse et al. | | 2005/0004564 A1 | 1/2005 | Wham et al. |
| 7,438,714 B2 * | 10/2008 | Phan ........................... 606/49 | | 2005/0004569 A1 | 1/2005 | Witt et al. |
| 7,442,193 B2 | 10/2008 | Shields et al. | | 2005/0033278 A1 | 2/2005 | McClurken et al. |
| 7,442,194 B2 | 10/2008 | Dumbauld et al. | | 2005/0059934 A1 | 3/2005 | Wenchell et al. |
| 7,445,621 B2 | 11/2008 | Dumbauld et al. | | 2005/0096645 A1 | 5/2005 | Wellman et al. |
| 7,458,972 B2 | 12/2008 | Keppel | | 2005/0101951 A1 | 5/2005 | Wham et al. |
| 7,473,253 B2 | 1/2009 | Dycus et al. | | 2005/0101952 A1 | 5/2005 | Lands et al. |
| 7,481,810 B2 | 1/2009 | Dumbauld et al. | | 2005/0113818 A1 | 5/2005 | Sartor et al. |
| 7,487,780 B2 | 2/2009 | Hooven | | 2005/0113819 A1 | 5/2005 | Wham et al. |
| 7,491,201 B2 | 2/2009 | Shields et al. | | 2005/0113826 A1 | 5/2005 | Johnson et al. |
| 7,491,202 B2 | 2/2009 | Odom et al. | | 2005/0149017 A1 | 7/2005 | Dycus |
| 7,500,975 B2 | 3/2009 | Cunningham et al. | | 2005/0149151 A1 | 7/2005 | Orszulak et al. |
| 7,510,556 B2 | 3/2009 | Nguyen et al. | | 2005/0154387 A1 | 7/2005 | Moses et al. |
| 7,513,898 B2 | 4/2009 | Johnson et al. | | 2005/0182482 A1 | 8/2005 | Wang et al. |
| 7,540,872 B2 | 6/2009 | Schechter et al. | | 2005/0187547 A1 | 8/2005 | Sugi |
| 7,549,995 B2 | 6/2009 | Schultz | | 2005/0197659 A1 | 9/2005 | Bahney |
| 7,553,312 B2 | 6/2009 | Tetzlaff et al. | | 2005/0203504 A1 | 9/2005 | Wham et al. |
| 7,553,371 B2 | 6/2009 | Dubrow et al. | | 2005/0261763 A1 | 11/2005 | Wang et al. |
| 7,553,686 B2 * | 6/2009 | George et al. ............... 438/48 | | 2005/0278020 A1 | 12/2005 | Wang et al. |
| 7,879,035 B2 * | 2/2011 | Garrison et al. ............ 606/51 | | 2006/0052778 A1 | 3/2006 | Chapman et al. |
| 2001/0014804 A1 | 8/2001 | Goble et al. | | 2006/0052779 A1 | 3/2006 | Hammill |
| 2002/0009604 A1 | 1/2002 | Zamora et al. | | 2006/0064085 A1 | 3/2006 | Schechter et al. |
| 2002/0013583 A1 | 1/2002 | Camran et al. | | 2006/0064086 A1 | 3/2006 | Odom |
| 2002/0022836 A1 | 2/2002 | Goble et al. | | 2006/0074417 A1 | 4/2006 | Cunningham et al. |
| 2002/0049442 A1 | 4/2002 | Roberts et al. | | 2006/0079888 A1 | 4/2006 | Mulier et al. |
| 2002/0099372 A1 | 7/2002 | Schulze et al. | | 2006/0079890 A1 | 4/2006 | Guerra |
| 2002/0107517 A1 | 8/2002 | Witt et al. | | 2006/0079891 A1 | 4/2006 | Arts et al. |
| 2002/0111624 A1 | 8/2002 | Witt et al. | | 2006/0079933 A1 | 4/2006 | Hushka et al. |
| 2002/0188294 A1 | 12/2002 | Couture et al. | | 2006/0084973 A1 | 4/2006 | Hushka |

| | | |
|---|---|---|
| 2006/0089670 A1 | 4/2006 | Hushka |
| 2006/0116675 A1 | 6/2006 | McClurken et al. |
| 2006/0129146 A1 | 6/2006 | Dycus et al. |
| 2006/0142853 A1 | 6/2006 | Wang et al. |
| 2006/0167450 A1 | 7/2006 | Johnson et al. |
| 2006/0167452 A1 | 7/2006 | Moses et al. |
| 2006/0173452 A1 | 8/2006 | Buysse et al. |
| 2006/0189981 A1 | 8/2006 | Dycus et al. |
| 2006/0190035 A1 | 8/2006 | Hushka et al. |
| 2006/0217709 A1 | 9/2006 | Couture et al. |
| 2006/0229666 A1 | 10/2006 | Suzuki et al. |
| 2006/0253126 A1 | 11/2006 | Bjerken et al. |
| 2006/0259032 A1 | 11/2006 | Nesbitt |
| 2006/0259033 A1 | 11/2006 | Nesbitt |
| 2006/0259036 A1 | 11/2006 | Tetzlaff et al. |
| 2006/0264922 A1 | 11/2006 | Sartor et al. |
| 2006/0264931 A1 | 11/2006 | Chapman et al. |
| 2006/0283093 A1 | 12/2006 | Petrovic et al. |
| 2006/0287641 A1 | 12/2006 | Perlin |
| 2007/0016182 A1 | 1/2007 | Lipson et al. |
| 2007/0016187 A1 | 1/2007 | Weinberg et al. |
| 2007/0027532 A1 | 2/2007 | Wang et al. |
| 2007/0043352 A1 | 2/2007 | Garrison et al. |
| 2007/0043353 A1 | 2/2007 | Dycus et al. |
| 2007/0060919 A1 | 3/2007 | Isaacson et al. |
| 2007/0062017 A1 | 3/2007 | Dycus et al. |
| 2007/0073130 A1 | 3/2007 | Finch et al. |
| 2007/0074807 A1 | 4/2007 | Guerra |
| 2007/0078456 A1 | 4/2007 | Dumbauld et al. |
| 2007/0078458 A1 | 4/2007 | Dumbauld et al. |
| 2007/0078459 A1 | 4/2007 | Johnson et al. |
| 2007/0088356 A1 | 4/2007 | Moses et al. |
| 2007/0093811 A1 | 4/2007 | Nesbitt |
| 2007/0106294 A1 | 5/2007 | Nesbitt |
| 2007/0106295 A1 | 5/2007 | Garrison et al. |
| 2007/0106297 A1 | 5/2007 | Dumbauld et al. |
| 2007/0118111 A1 | 5/2007 | Weinberg |
| 2007/0118113 A1 | 5/2007 | Nesbitt |
| 2007/0118115 A1 | 5/2007 | Artale et al. |
| 2007/0123853 A1 | 5/2007 | Nesbitt |
| 2007/0128240 A1 | 6/2007 | Krulevitch |
| 2007/0129726 A1 | 6/2007 | Eder et al. |
| 2007/0142833 A1 | 6/2007 | Dycus et al. |
| 2007/0142834 A1 | 6/2007 | Dumbauld |
| 2007/0156139 A1 | 7/2007 | Schechter et al. |
| 2007/0156140 A1 | 7/2007 | Baily |
| 2007/0173811 A1 | 7/2007 | Couture et al. |
| 2007/0173814 A1 | 7/2007 | Hixson et al. |
| 2007/0179499 A1 | 8/2007 | Garrison |
| 2007/0185482 A1 | 8/2007 | Eder et al. |
| 2007/0198011 A1 | 8/2007 | Sugita |
| 2007/0213712 A1 | 9/2007 | Buysse et al. |
| 2007/0225699 A1 | 9/2007 | Goble et al. |
| 2007/0225707 A1 | 9/2007 | Wisnewski et al. |
| 2007/0255279 A1 | 11/2007 | Buysse et al. |
| 2007/0260235 A1 | 11/2007 | Podhajsky |
| 2007/0260238 A1 | 11/2007 | Guerra |
| 2007/0260241 A1 | 11/2007 | Dalla Betta et al. |
| 2007/0260242 A1 | 11/2007 | Dycus et al. |
| 2007/0265616 A1 | 11/2007 | Couture et al. |
| 2007/0282247 A1 | 12/2007 | Desai et al. |
| 2008/0004616 A1 | 1/2008 | Patrick |
| 2008/0004670 A1 | 1/2008 | McVenes et al. |
| 2008/0009860 A1 | 1/2008 | Odom |
| 2008/0015575 A1 | 1/2008 | Odom et al. |
| 2008/0021450 A1 | 1/2008 | Couture |
| 2008/0033428 A1 | 2/2008 | Artale et al. |
| 2008/0038170 A1 | 2/2008 | Sandhage et al. |
| 2008/0039835 A1 | 2/2008 | Johnson et al. |
| 2008/0039836 A1 | 2/2008 | Odom et al. |
| 2008/0045947 A1 | 2/2008 | Johnson et al. |
| 2008/0050509 A1 | 2/2008 | Nesbitt |
| 2008/0058802 A1 | 3/2008 | Couture et al. |
| 2008/0077131 A1 | 3/2008 | Yates et al. |
| 2008/0082100 A1 | 4/2008 | Orton et al. |
| 2008/0091189 A1 | 4/2008 | Carlton |
| 2008/0114356 A1 | 5/2008 | Johnson et al. |
| 2008/0167651 A1 | 7/2008 | Tetzlaff et al. |
| 2008/0195093 A1 | 8/2008 | Couture et al. |
| 2008/0195170 A1 | 8/2008 | Asgari |
| 2008/0215051 A1 | 9/2008 | Buysse et al. |
| 2008/0221565 A1 | 9/2008 | Eder et al. |
| 2008/0228179 A1 | 9/2008 | Eder et al. |
| 2008/0243120 A1 | 10/2008 | Lawes et al. |
| 2008/0249527 A1 | 10/2008 | Couture |
| 2008/0312653 A1 | 12/2008 | Arts et al. |
| 2008/0319442 A1 | 12/2008 | Unger et al. |
| 2009/0012520 A1 | 1/2009 | Hixson et al. |
| 2009/0018535 A1 | 1/2009 | Schechter et al. |
| 2009/0024126 A1 | 1/2009 | Artale et al. |
| 2009/0043304 A1 | 2/2009 | Tetzlaff et al. |
| 2009/0048596 A1 | 2/2009 | Shields et al. |
| 2009/0062794 A1 | 3/2009 | Buysse et al. |
| 2009/0082766 A1 | 3/2009 | Unger et al. |
| 2009/0082767 A1 | 3/2009 | Unger et al. |
| 2009/0082769 A1 | 3/2009 | Unger et al. |
| 2009/0088738 A1 | 4/2009 | Guerra et al. |
| 2009/0088739 A1 | 4/2009 | Hushka et al. |
| 2009/0088740 A1 | 4/2009 | Guerra et al. |
| 2009/0088741 A1 | 4/2009 | Hushka et al. |
| 2009/0088744 A1 | 4/2009 | Townsend |
| 2009/0088745 A1 | 4/2009 | Hushka et al. |
| 2009/0088746 A1 | 4/2009 | Hushka et al. |
| 2009/0088747 A1 | 4/2009 | Hushka et al. |
| 2009/0088748 A1 | 4/2009 | Guerra et al. |
| 2009/0088749 A1 | 4/2009 | Hushka et al. |
| 2009/0088750 A1 | 4/2009 | Hushka et al. |
| 2009/0112206 A1 | 4/2009 | Dumbauld et al. |
| 2009/0131934 A1 | 5/2009 | Odom et al. |
| 2009/0149853 A1 | 6/2009 | Shields et al. |
| 2009/0149854 A1 | 6/2009 | Cunningham et al. |
| 2009/0171350 A1 | 7/2009 | Dycus et al. |
| 2009/0171353 A1 | 7/2009 | Johnson et al. |
| 2009/0182323 A1 | 7/2009 | Eder et al. |
| 2009/0182327 A1 | 7/2009 | Unger |
| 2009/0187188 A1 | 7/2009 | Guerra et al. |
| 2010/0055795 A1 | 3/2010 | Lee |
| 2010/0069904 A1 | 3/2010 | Cunningham |
| 2010/0092537 A1 | 4/2010 | Strömme |

FOREIGN PATENT DOCUMENTS

| | | |
|---|---|---|
| DE | 2415263 | 10/1975 |
| DE | 2514501 | 10/1976 |
| DE | 2627679 | 1/1977 |
| DE | 3612646 | 4/1987 |
| DE | 8712328 | 3/1988 |
| DE | 4303882 | 8/1994 |
| DE | 4403252 | 8/1995 |
| DE | 19515914 | 7/1996 |
| DE | 29616210 | 1/1997 |
| DE | 19608716 | 4/1997 |
| DE | 19751106 | 5/1998 |
| DE | 19751108 | 5/1999 |
| DE | 19738457 | 1/2009 |
| EP | 0364216 | 4/1990 |
| EP | 0467501 | 1/1992 |
| EP | 0518230 | 12/1992 |
| EP | 0541930 | 5/1993 |
| EP | 0572131 | 12/1993 |
| EP | 0584787 | 3/1994 |
| EP | 0589453 | 3/1994 |
| EP | 0589555 | 3/1994 |
| EP | 0623316 | 11/1994 |
| EP | 0624348 | 11/1994 |
| EP | 0650701 | 5/1995 |
| EP | 0694290 | 3/1996 |
| EP | 0717966 | 6/1996 |
| EP | 0754437 | 3/1997 |
| EP | 0517243 | 9/1997 |
| EP | 0853922 | 7/1998 |
| EP | 0875209 | 11/1998 |
| EP | 0878169 | 11/1998 |
| EP | 0887046 | 1/1999 |
| EP | 0923907 | 6/1999 |
| EP | 0986990 | 3/2000 |
| EP | 1034747 | 9/2000 |
| EP | 1034748 | 9/2000 |
| EP | 1025807 | 10/2000 |

| | | |
|---|---|---|
| EP | 1034746 | 10/2000 |
| EP | 1050278 | 11/2000 |
| EP | 1053719 | 11/2000 |
| EP | 1053720 | 11/2000 |
| EP | 1055399 | 11/2000 |
| EP | 1055400 | 11/2000 |
| EP | 1080694 | 3/2001 |
| EP | 1082944 | 3/2001 |
| EP | 1159926 | 12/2001 |
| EP | 1177771 | 2/2002 |
| EP | 1301135 | 4/2003 |
| EP | 1330991 | 7/2003 |
| EP | 0852480 | 8/2003 |
| EP | 1486177 | 6/2004 |
| EP | 1472984 | 11/2004 |
| EP | 0774232 | 1/2005 |
| EP | 1527747 | 5/2005 |
| EP | 1530952 | 5/2005 |
| EP | 1532932 | 5/2005 |
| EP | 1158919 | 6/2005 |
| EP | 1535581 | 6/2005 |
| EP | 1330990 | 10/2005 |
| EP | 1158917 | 11/2005 |
| EP | 1609430 | 12/2005 |
| EP | 1632192 | 3/2006 |
| EP | 1642543 | 4/2006 |
| EP | 1645238 | 4/2006 |
| EP | 1645240 | 4/2006 |
| EP | 1649821 | 4/2006 |
| EP | 1253866 | 7/2006 |
| EP | 1707143 | 10/2006 |
| EP | 1795227 | 11/2006 |
| EP | 1769765 | 4/2007 |
| EP | 1769766 | 4/2007 |
| EP | 1040793 | 5/2007 |
| EP | 1905370 | 4/2008 |
| EP | 1929970 | 6/2008 |
| EP | 1683496 | 12/2008 |
| GB | 623316 | 5/1949 |
| GB | 1490585 | 11/1977 |
| GB | 2214430 A | 6/1989 |
| GB | 2213416 A | 8/1989 |
| JP | 61-501068 | 9/1984 |
| JP | 65-502328 | 3/1992 |
| JP | 5-5106 | 1/1993 |
| JP | 5-40112 | 2/1993 |
| JP | 06343644 A2 | 12/1994 |
| JP | 07265328 A2 | 10/1995 |
| JP | 08056955 A2 | 3/1996 |
| JP | 08252263 A2 | 10/1996 |
| JP | 09010223 A2 | 1/1997 |
| JP | 11244298 A2 | 9/1999 |
| JP | 2000-342599 A2 | 12/2000 |
| JP | 2000-350732 A2 | 12/2000 |
| JP | 2001-008944 A2 | 1/2001 |
| JP | 2001-029356 A2 | 2/2001 |
| JP | 2001-128990 A2 | 5/2001 |
| JP | 2008229348 | 10/2008 |
| SU | 401367 | 11/1974 |
| WO | WO 89/00757 | 1/1989 |
| WO | WO 92/04873 | 4/1992 |
| WO | WO 92/06642 | 4/1992 |
| WO | WO 93/21845 | 11/1993 |
| WO | WO 9407272 | 3/1994 |
| WO | WO 94/08524 | 4/1994 |
| WO | WO 94/20025 | 9/1994 |
| WO | WO 95/02369 | 1/1995 |
| WO | WO 95/07662 | 3/1995 |
| WO | WO 95/15124 | 6/1995 |
| WO | WO 9526833 | 10/1995 |
| WO | WO 96/05776 | 2/1996 |
| WO | WO 96/22056 | 7/1996 |
| WO | WO 9620652 | 7/1996 |
| WO | WO 96/13218 | 9/1996 |
| WO | WO 97/00646 | 1/1997 |
| WO | WO 97/00647 | 1/1997 |
| WO | WO 97/10764 | 3/1997 |
| WO | WO 9711649 | 4/1997 |
| WO | WO 97/24073 | 7/1997 |
| WO | WO 97/24993 | 7/1997 |
| WO | WO 98/27880 | 7/1998 |
| WO | WO 9855037 | 12/1998 |
| WO | WO 99/03407 | 1/1999 |
| WO | WO 99/03408 | 1/1999 |
| WO | WO 99/03409 | 1/1999 |
| WO | WO 99/12488 | 3/1999 |
| WO | WO 99/23933 | 5/1999 |
| WO | WO 99/40857 | 8/1999 |
| WO | WO 99/40861 | 8/1999 |
| WO | WO 99/51158 | 10/1999 |
| WO | WO 99/66850 | 12/1999 |
| WO | WO 9962414 | 12/1999 |
| WO | WO 00/24330 | 5/2000 |
| WO | WO 00/24331 | 5/2000 |
| WO | WO 00/36986 | 6/2000 |
| WO | WO 00/41638 | 7/2000 |
| WO | WO 00/47124 | 8/2000 |
| WO | WO 00/53112 | 9/2000 |
| WO | WO 0053112 | 9/2000 |
| WO | WO 0053113 | 9/2000 |
| WO | WO 01/17448 | 3/2001 |
| WO | WO 01/54604 | 8/2001 |
| WO | WO 0158371 | 8/2001 |
| WO | WO 02/07627 | 1/2002 |
| WO | WO 02/067798 | 9/2002 |
| WO | WO 02/080783 | 10/2002 |
| WO | WO 02/080784 | 10/2002 |
| WO | WO 02/080785 | 10/2002 |
| WO | WO 02/080786 | 10/2002 |
| WO | WO 02/080793 | 10/2002 |
| WO | WO 02/080794 | 10/2002 |
| WO | WO 02/080795 | 10/2002 |
| WO | WO 02/080796 | 10/2002 |
| WO | WO 02/080797 | 10/2002 |
| WO | WO 02/080798 | 10/2002 |
| WO | WO 02/080799 | 10/2002 |
| WO | WO 02/081170 | 10/2002 |
| WO | WO 03/061500 | 7/2003 |
| WO | WO 03/090630 | 11/2003 |
| WO | WO 03/101311 | 12/2003 |
| WO | WO 2004/032776 | 4/2004 |
| WO | WO 2004/032777 | 4/2004 |
| WO | WO 2004030706 | 4/2004 |
| WO | WO 2004/052221 | 6/2004 |
| WO | WO 2004/073488 | 9/2004 |
| WO | WO 2004/073490 | 9/2004 |
| WO | WO 2004/073753 | 9/2004 |
| WO | WO 2004/082495 | 9/2004 |
| WO | WO 2004/098383 | 11/2004 |
| WO | WO 2004/103156 | 12/2004 |
| WO | WO 2005/004734 | 1/2005 |
| WO | WO 2005/004735 | 1/2005 |
| WO | WO 2005046470 | 5/2005 |
| WO | WO 2005/110264 | 11/2005 |
| WO | WO 2006049753 | 5/2006 |
| WO | WO 2006102235 | 9/2006 |
| WO | WO 2006127474 | 11/2006 |
| WO | WO 2006133365 | 12/2006 |
| WO | WO 2007078304 | 7/2007 |
| WO | WO 2008/045348 | 4/2008 |
| WO | WO 2008/045350 | 4/2008 |
| WO | WO 2008056323 | 5/2008 |
| WO | WO 2008085886 | 7/2008 |
| WO | WO 2008097808 | 8/2008 |
| WO | WO 2008098924 | 8/2008 |
| WO | WO 2009009157 | 1/2009 |
| WO | WO 2009091384 | 7/2009 |
| WO | WO 2009098658 | 8/2009 |
| WO | WO 2010014261 | 2/2010 |
| WO | WO 2010042750 | 4/2010 |

OTHER PUBLICATIONS

Chung et al., "Clinical Experience of Sutureless Closed Hemorrhoidectomy with LigaSure" Diseases of the Colon & Rectum vol. 46, No. 1 Jan. 2003.

Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J.Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
Int'l Search Report EP 98944778 dated Oct. 31, 2000.
Int'l Search Report EP 98957771 dated Aug. 9, 2001.
Int'l Search Report EP 98958575.7 dated Sep. 20, 2002.
Int'l Search Report EP 04013772 dated Apr. 1, 2005.
Int'l Search Report EP 04027314 dated Mar. 10, 2005.
Int'l Search Report EP 04027479 dated Mar. 8, 2005.
Int'l Search Report EP 04027705 dated Feb. 3, 2005.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05013463.4 dated Sep. 28, 2005.
Int'l Search Report EP 05013895 dated Oct. 14, 2005.
Int'l Search Report EP 05016399 dated Jan. 5, 2006.
Int'l Search Report EP 05017281 dated Nov. 16, 2005.
Int'l Search Report EP 05019130.3 dated Oct. 18, 2005.
Int'l Search Report EP 05019429.9 dated May 6, 2008.
Int'l Search Report EP 05020665.5 dated Feb. 16, 2006.
Int'l Search Report EP 05020666.3 dated Feb. 17, 2006.
Int'l Search Report EP 05021197.8 dated Jan. 31, 2006.
Int'l Search Report EP 05021779.3 dated Jan. 18, 2006.
Int'l Search Report EP 05021780.1 dated Feb. 9, 2006.
Int'l Search Report EP 05021937.7 dated Jan. 13, 2006.
Int'l Search Report—extended—EP 05021937.7 dated Mar. 6, 2006.
Int'l Search Report EP 05023017.6 dated Feb. 16, 2006.
Int'l Search Report EP 06002279.5 dated Mar. 22, 2006.
Int'l Search Report EP 06005185.1 dated Apr. 18, 2006.
Int'l Search Report EP 06006716 dated Aug. 4, 2006.
Int'l Search Report EP 06008515.6 dated Jan. 8, 2009.
Int'l Search Report EP 06008779.8 dated Jun. 13, 2006.
Int'l Search Report EP 06014461.5 dated Oct. 20, 2006.
Int'l Search Report EP 06020574.7 dated Sep. 21, 2007.
Int'l Search Report EP 06020583.8 dated Jan. 30, 2007.
Int'l Search Report EP 06020584.6 dated Jan. 12, 2007.
Int'l Search Report EP 06020756.0 dated Feb. 5, 2007.
Int'l Search Report EP 06 024122.1 dated Mar. 19, 2007.
Int'l Search Report EP 06024123.9 dated Feb. 26, 2007.
Int'l Search Report EP 07 001480.8 dated Apr. 12, 2007.
Int'l Search Report EP 07 001488.1 dated May 29, 2007.
Int'l Search Report EP 07 009026.1 dated Sep. 12, 2007.
Int'l Search Report Extended—EP 07 009029.5 dated Jul. 12, 2007.
Int'l Search Report EP 07 009321.6 dated Aug. 17, 2007.

Int'l Search Report EP 07 010672.9 dated Oct. 1, 2007.
Int'l Search Report EP 07 013779.9 dated Oct. 18, 2007.
Int'l Search Report EP 07 014016 dated Jan. 28, 2008.
Int'l Search Report EP 07 015191.5 dated Dec. 19, 2007.
Int'l Search Report EP 07 015601.3 dated Dec. 6, 2007.
Int'l Search Report EP 07 020283.3 dated Jan. 16, 2008.
Int'l Search Report EP 07 021646.0 dated Jul. 9, 2008.
Int'l Search Report EP 07 021647.8 dated May 2, 2008.
Int'l Search Report EP 08 02692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report PCT/US98/18640 dated Dec. 17, 1998.
Int'l Search Report PCT/US98/23950 dated Dec. 29, 1998.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 3, 2001.
International Search Report PCT/US01/11224 dated Nov. 13, 2001.
Int'l Search Report PCT/US01/11340 dated Aug. 7, 2001.
Int'l Search Report PCT/US01/11420 dated Oct. 8, 2001.
Int'l Search Report PCT/US02/01890 dated Jul. 17, 2002.
Int'l Search Report PCT/US02/11100 dated Jul. 9, 2002.
Int'l Search Report PCT/US03/28534 dated Dec. 19, 2003.
Int'l Search Report PCT/US04/03436 dated Oct. 5, 2004.
Int'l Search Report PCT/US04/13273 dated Nov. 22, 2004.
Int'l Search Report PCT/US04/15311 dated Nov. 18, 2004.
Int'l Search Report PCT/US07/021438 dated Apr. 1, 2008.
Int'l Search Report PCT/US07/021440 dated Apr. 8, 2008.
Int'l Search Report PCT/US08/61498 dated Sep. 22, 2008.
Herrmann et al., "Conformal Hydrophobic Coatings Prepared Using Atomic Layer Deposition Seed Layers and Non-chlorinated Hydrophobic Precursors", J. Micromech. Microeng. 15 (2005) pp. 1-9.
Int'l Search Report EP 09 152267.2 Dated Jun. 15, 2009.
Int'l Search Report EP 09 152898.4 Dated Jun. 10, 2009.
Int'l Search Report PCT/US09/032690 dated Jun. 16, 2009.

* cited by examiner

ELECTROSURGICAL INSTRUMENT HAVING A COATED ELECTRODE UTILIZING AN ATOMIC LAYER DEPOSITION TECHNIQUE

BACKGROUND

1. Technical Field

The present disclosure relates generally to an electrosurgical system for treating tissue. More particularly, the present disclosure is directed to an electrosurgical instrument having a coated electrode utilizing an atomic layer deposition technique.

2. Background of Related Art

Electrosurgery involves the application of electricity and/or electromagnetic energy to cut, dissect, ablate, coagulate, seal, or otherwise treat biological tissue during a surgical procedure. Additionally, certain electrosurgical modes invoke the application of electrosurgical energy through a compressed vessel secured between two electrodes to seal the vessel without significant cutting during the sealing process. Electrosurgical cutting, on the other hand, includes applying an electrical spark to tissue in order to produce a cutting or dividing effect. Blending includes the function of cutting combined with the production of a hemostasis effect.

Generally, electrosurgery utilizes an energy generator, an active electrode and a return electrode. The energy generator generates an electromagnetic wave (commonly referred to as "electrosurgical energy"), typically above 100 kilohertz to avoid muscle and/or nerve stimulation between the active and return electrodes when applied to tissue. During electrosurgery, current generated by the electrosurgical generator is conducted through the patient's tissue disposed between the two electrodes. The electrosurgical energy is returned to the electrosurgical source via a return electrode pad positioned under a patient (e.g., a monopolar system configuration) or a smaller return electrode positionable in bodily contact with or immediately adjacent to the surgical site (e.g., a bipolar system configuration). The current causes the tissue to heat up as the electromagnetic wave overcomes the tissue's impedance.

As mentioned above, vessel sealing invokes the application of electrosurgical energy thorough a compressed vessel secured between two electrodes to seat the vessel without significant cutting during the sealing process. The tissue undergoes changes by the applied electrosurgical energy including tissue in direct contact with the electrodes. The tissue in contact with the electrodes sometimes sticks to the electrodes and so called "eschar" can build up on the electrodes. The eschar must be cleaned or sticking will worsen. Eschar increases the impedance between the electrode and the tissue being treated thus reducing the efficiency of the electrosurgical energy transfer. Also, overall tissue impedance is typically monitored during sealing and the build up of eschar can contribute to higher impedance measurements resulting in increased sealing time. Therefore, a non-stick coating is typically applied to the electrodes to mitigate these effects and to reduce stiction.

SUMMARY

The present disclosure relates generally to an electrosurgical system for treating tissue. More particularly, the present disclosure is directed to an electrosurgical instrument having electrode with a coating formed using an atomic layer deposition technique. An ALD coating can be applied to any electrode surface including monopolar electrosurgical devices or bipolar forceps used for cutting, coagulating, ablating. Additionally, an ALD coating may be applied to a return electrode of an electrosurgical system.

In an embodiment of the present disclosure, an electrosurgical instrument includes one or more support members and an electrode. The electrode is disposed on a support member. A coating is disposed (at least partially) on the electrode. The coating includes a seed layer and an ALD layer, which may be either hydrophobic or hydrophilic.

In another embodiment of the present disclosure, the seed layer is also formed using atomic layer deposition. The seed layer may be conductive or insulative; and additionally or alternatively, the seed layer may be ceramic. The seed layer can include $Al_2O_3$ formed from sequential reactions shown below as reactions (I) and (II).

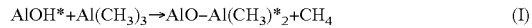

$$AlOH^* + Al(CH_3)_3 \rightarrow AlO-Al(CH_3)^*_2 + CH_4 \quad (I)$$

$$AlCH^*_3 + H_2O \rightarrow AlOH^* + CH_4 \quad (II)$$

The ALD layer may be formed using one or more precursors such as a chlorosilanes precursor, a non-chlorinated hydrophobic precursor, an alkylaminosilane precursor, a chlorosilane precursor, a bis-alkylaminosilane precursor and/or a tris-alkylaminosilane precursor.

In yet another embodiment, the seed layer includes titanium nitride and the ALD layer includes $Zn_{19}Al_5O_2$. Alternatively, either the seed layer or the ALD layer includes $Zn_{19}Al_5O_2$. Additionally or attentively, the seed layer includes about 5% of titania-alumina-oxide and the ALD layer includes about 90% titania. The seed layer may have surface functional groups, such as surface hydroxyl groups such that the function groups react with the hydroxyl groups to form the ALD layer. The ALD layer may be formed from Tridecafluoro-1,1,2,2-tetrahydrooctylmethyl-bis(dimethylamino)silane(FOMB(DMAS)S, $C_8F_{13}H_4(CH_3)Si(N(CH_2)_2)_2)$.

In yet another embodiment of the present disclosure, a method of coating includes: providing an electrosurgical instrument; coating an electrode of the electrosurgical instrument with a seed layer; and coating the seed layer with an ALD layer such that the ALD layer is hydrophobic or hydrophilic. The method may also include applying first and second precursors to the electrode such that the second precursor reacts with the first precursor to form (or partially form) the seed layer. The first precursor may be trimethylaluminum ($Al(CH_3)_3$, TMA) and the second precursor may be $H_2O$. Additionally or alternatively, the method includes applying a precursor to the seed layer forming the ALD layer, such as Tridecafluoro-1,1,2,2-tetrahydrooctylmethyl-bis(dimethylamino)silane(FOMB(DMAS)S, $C_8F_{13}H_4(CH_3)Si(N(CH_2)_2)_2)$.

BRIEF DESCRIPTION OF THE DRAWINGS

Various embodiments are described herein with reference to the drawings wherein.

DETAILED DESCRIPTION

Particular embodiments of the present disclosure are described hereinbelow with reference to the accompanying drawings. In the following description, well-known functions or constructions are not described in detail to avoid obscuring the present disclosure in unnecessary detail.

Figure 1A:
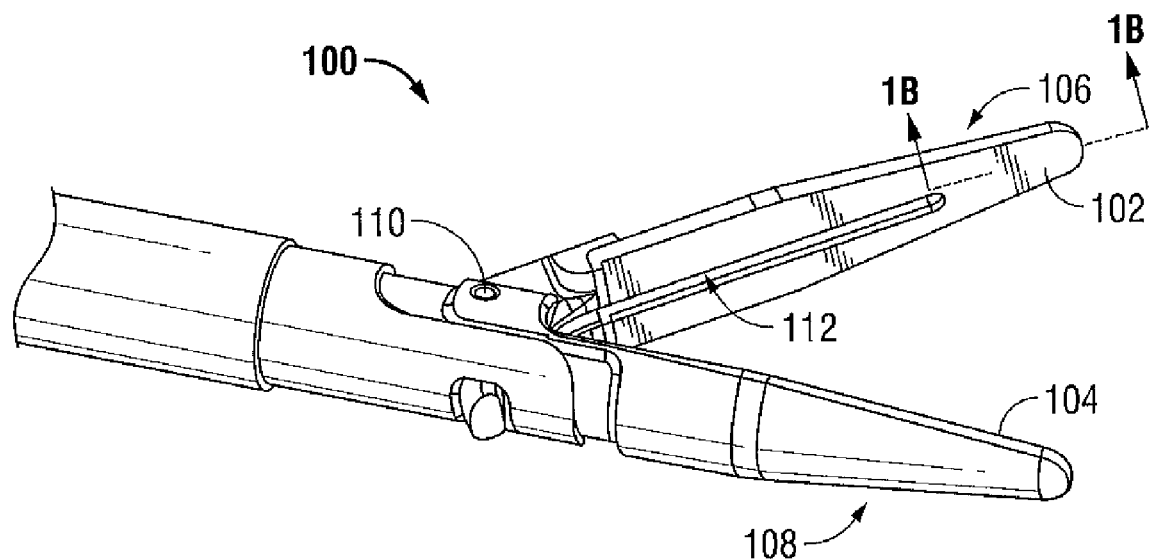
FIG. 1A is perspective-view of an electrosurgical instrument having coated electrodes in accordance with an embodiment of the present disclosure.

Referring to the drawings, FIG. 1A is a perspective-view of an electrosurgical instrument 100 having coated electrodes 102 and 104 in accordance with the present disclosure. Although the coating is discussed with regards to electrosurgical forceps, it is in the purview of one of ordinary skill in the art to extend the coating system and method to other instruments, including: monopolar or bipolar electrosurgical instruments, return pads, RF ablation probes, microwave surgical instruments, and the like.

Electrosurgical instrument 100 may seal vessels using electrosurgical energy and includes jaw members 106 and 108 that are movable relative to each other about pivot 110 to grasp tissue. Jaw member 106 supports coated electrode 102 and jaw member 108 supports coated electrode 104. Jaw member 106 defines a channel 112 allowing reciprocating actuation of a cutting device (not shown), such as a blade or cutting electrode. Jaw member 108 may also include a channel, which is not explicitly shown in FIG. 1A.

During an electrosurgical procedure, a blood vessel (not shown) is placed between jaw members 106 and 108 while jaw member 106 is in an "open" position (as shown in FIG. 1), that is, jaw member 106 is spaced apart from jaw member 108. The surgeon actuates one or more suitable mechanical linkages (not shown) causing jaw member 106 to pivot about pivot pin 110 towards jaw member 108, thereby grasping the vessel. The surgeon thereafter can activate an electrosurgical generator (not shown) causing electrosurgical energy to flow between coated electrodes 102 and 104 through the grasped vessel. The tissue of the vessel heats up as the electrosurgical energy overcomes impedance of the tissue in the vessel. The electrosurgical energy seals the vessel thus stopping blood flow therethrough.

During vessel sealing, tissue tends to stick to non-coated electrodes and tissue eschar tends to buildup on the non-coated electrodes, which detrimentally affects the overall seal quality due to the eschar increasing the impedance between electrodes. The increase in impedance may provide unreliable feedback to the electrosurgical generator. By coating electrodes with a non-stick coating, many of these effects are mitigated and a better seal results. According to the teaching of the present disclosure, a non-stick coating is deposited (or formed) on electrodes utilizing atomic layer deposition.

Atomic Layer Deposition (referred to herein as "ALD") is a gas phase chemical process used to create thin coatings. The majority of ALD reactions use two chemicals, typically called precursors to form these coatings. These precursors react individually with each surface in a repeatable and sequential manner. Film growth is controlled by exposing the precursors to a growth surface repeatedly. Generally, ALD is a self-limiting, sequential surface chemistry that deposits conformal films or coatings onto substrates of varying compositions. ALD growth is based on surface reactions making atomic scale deposition control possible.

Figure 1B:
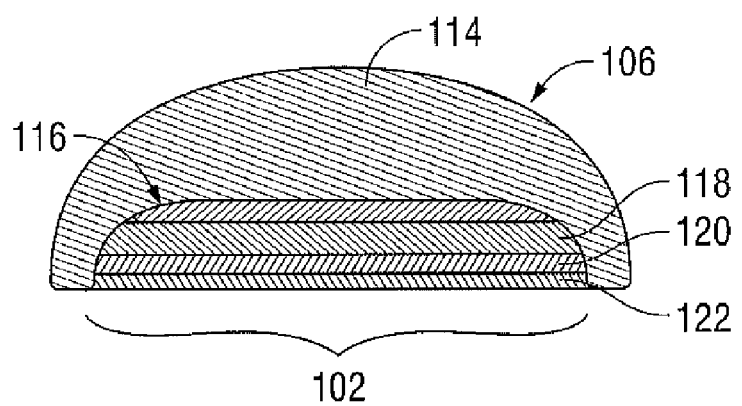
FIG. 1B is a cross-sectional view along line 1B-1B of the electrosurgical instrument of FIG. 1A in accordance with an embodiment of the present disclosure.
Figure 2A:
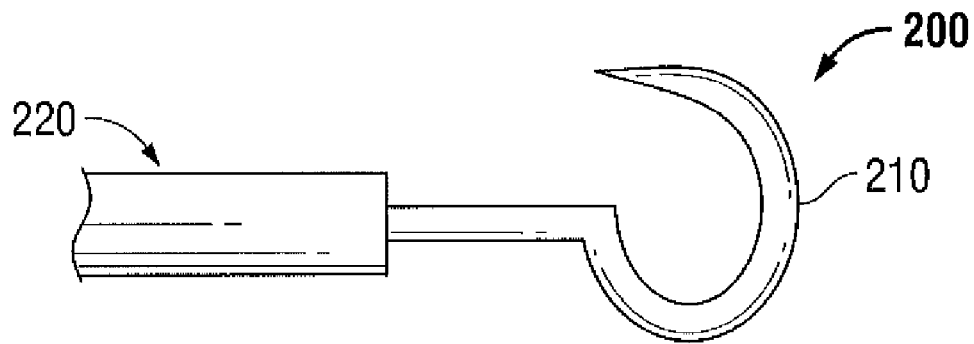
FIG. 2A-2E are various embodiments of electrosurgical instruments having a seed layer and a ALD layer disposed on a respective electrode in accordance with an embodiment of the present disclosure.
Figure 2B:
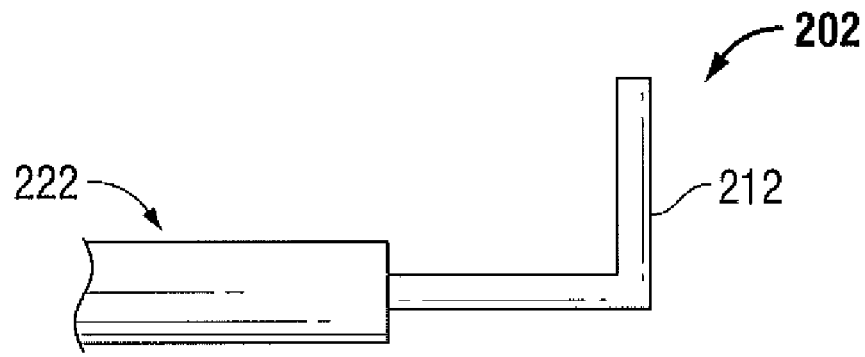
Figure 2C:
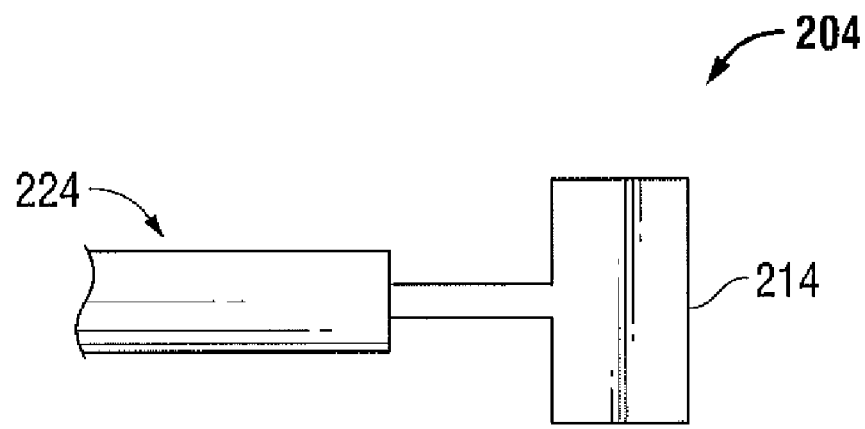
Figure 2D:
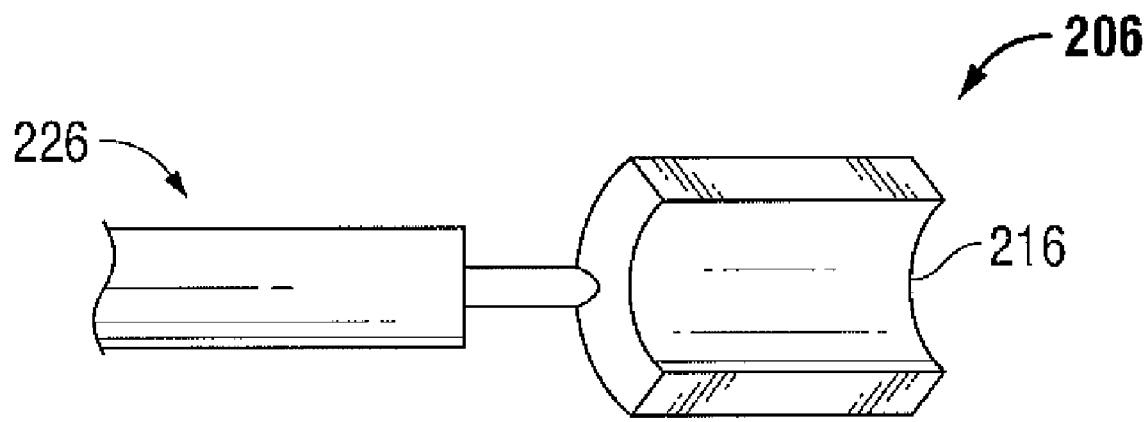
Figure 2E:
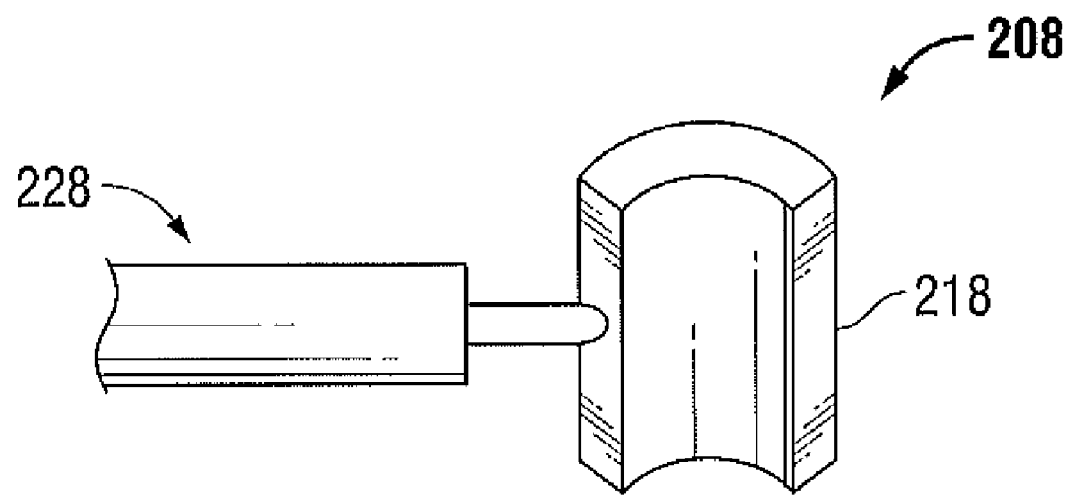

Referring to the drawings, FIG. 1B is a cross-sectional view along line 1B-1B of the electrosurgical instrument 100 as shown in FIG. 1A in accordance with the present disclosure. More particularly, FIG. 1B shows a cross-sectional view of jaw member 106. Coated electrode 102 is secured to a base 114 of jaw member 106 using a securing layer 116. Securing layer 114 is formed from any sufficient material for securing coated electrode 102 to support structure 114, such as glue, ceramic, silicon, epoxy, and the like. Additionally or alternatively, a securing device (not shown) may be used to secure coated electrode 102 to support structure 114, such as an oversold, a fastener, a clip, a screw, and the like. Coated electrode 102 includes an electrode 118, a seed layer 120, and an ALD layer 122. Coated electrode 102 may be capacitive and/or non-capacitive, and may have any sufficient operational bandwidth, e.g., from DC to radio frequencies.

Seed layer 120 may be conductive or insulative, and may be a ceramic. Seed layer 120 is formed on electrode 118 using atomic layer deposition. In one embodiment, seed layer 120 may be $Al_2O_3$ formed from one or more reactions using precursors. The overall binary reaction is $2Al(CH_3)_3 + 3H_2O \rightarrow Al_2O_3 + 6CH_4$ and is divided into two reactions shown as reactions 1 and 2 below:

$$AlOH^* + Al(CH_3)_3 \rightarrow AlO-Al(CH_3)_2^* + CH_4 \quad (1)$$

$$AlCH_3^* + H_2O \rightarrow AlOH^* + CH_4 \quad (2)$$

The asterisk denotes the surface species. These and other related reactions are discussed in an article in *The Journal of Micromechanics and Microengineering*, entitled "Conformal hydrophobic coatings prepared using atomic layer deposition seed layers and non-chlorinated hydrophobic precursors" by Herrmann, DelRio, Bright and George, which is hereby incorporated by reference in its entirety. Electrode 118 has surface hydroxyl groups in such that a precursor reacts therewith, such as trimethylaluminim ($Al(CH_3)_3$, TMA). Additionally or alternatively, the ALD layer 122 includes titanium nitride. The seed layer may also contain about 5% of titania-alumina-oxide.

Coated electrode 102 also includes an ALD layer 122. The ALD layer 122 is hydrophobic if seed layer 120 is insulative because water reduces the conductivity near coated electrode 102 or the ALD layer 122 is hydrophilic if seed layer 120 is conductive because increased conductivity is desirable. The ALD layer 122 is formed using one or more precursor, such as a chlorosilanes precursor, a non-chlorinated hydrophoblic precursor, an alkylaminosilane precursor, a chlorosilane precursor, a bis-alkylaminosilane precursor and a tris-alkylaminosilane precursor. Additionally or alternatively, ALD layer 122 is a ceramic.

After seed layer 120 is disposed on electrode 118 the ALD layer 122 is formed on the seed layer 120 by reacting with function groups of seed layer 120, such as surface hydroxyl groups on seed layer 120 which react with a precursor to form ALD layer 122. The ALD layer 120 may be formed from Tridecafluoro-1,1,2,2-tetrahydrooctylmethyl-bis(dimethylamino)silane (FOMB(DMAS)S, $C_8F_{13}H_4(CH_3)Si(N(CH_2)_2)_2)$. Additionally or alternatively, the ALD layer 120 may be about 90% titania. ALD layer 122 prevents and or mitigates the effects of tissue sticking to the surface of coated electrode 102 because of the ALD's chemical properties.

Referring to the drawings, FIGS. 2A-2E shows several electrosurgical instruments having a coated electrode. Although in FIG. 1 electrosurgical forceps were described as having a coating formed using atomic layer deposition, FIGS.

2A through 2E show several additional electrosurgical instruments that are coated using atomic layer deposition. Instruments 200 through 208 are shown and include support members 220 thorough 228. Each of support members 220 through 228 includes one of electrodes 210 through 218, respectively. Electrodes 210 through 218 may each either be hydrophilic or hydrophobic and may include a seed layer.

Figure 3A:
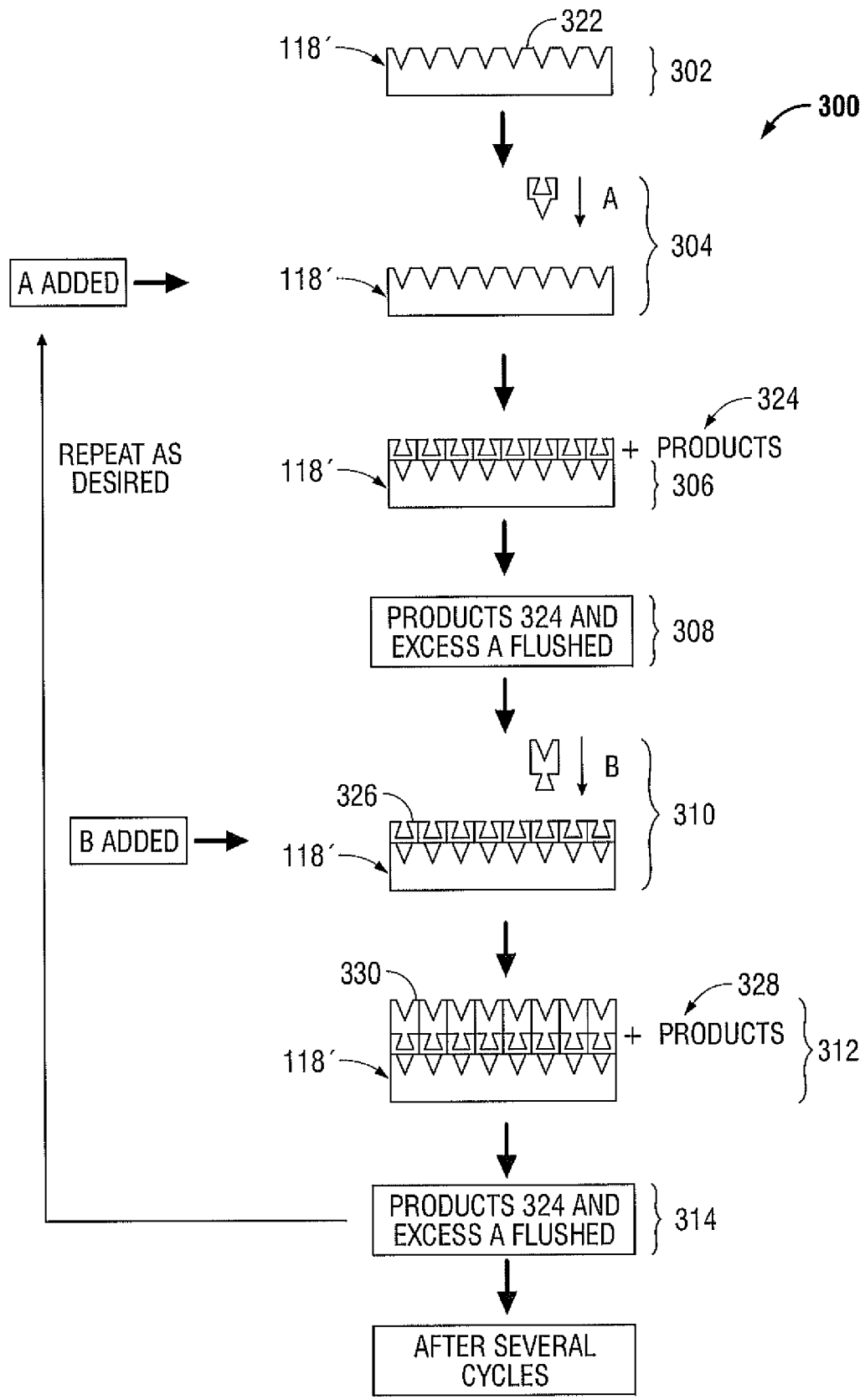
FIGS. 3A-3B is an illustration of various stages of disposing a seed layer and a ALD layer on an electrode using atomic layer deposition in accordance with an embodiment of the present disclosure.
Figure 3B:
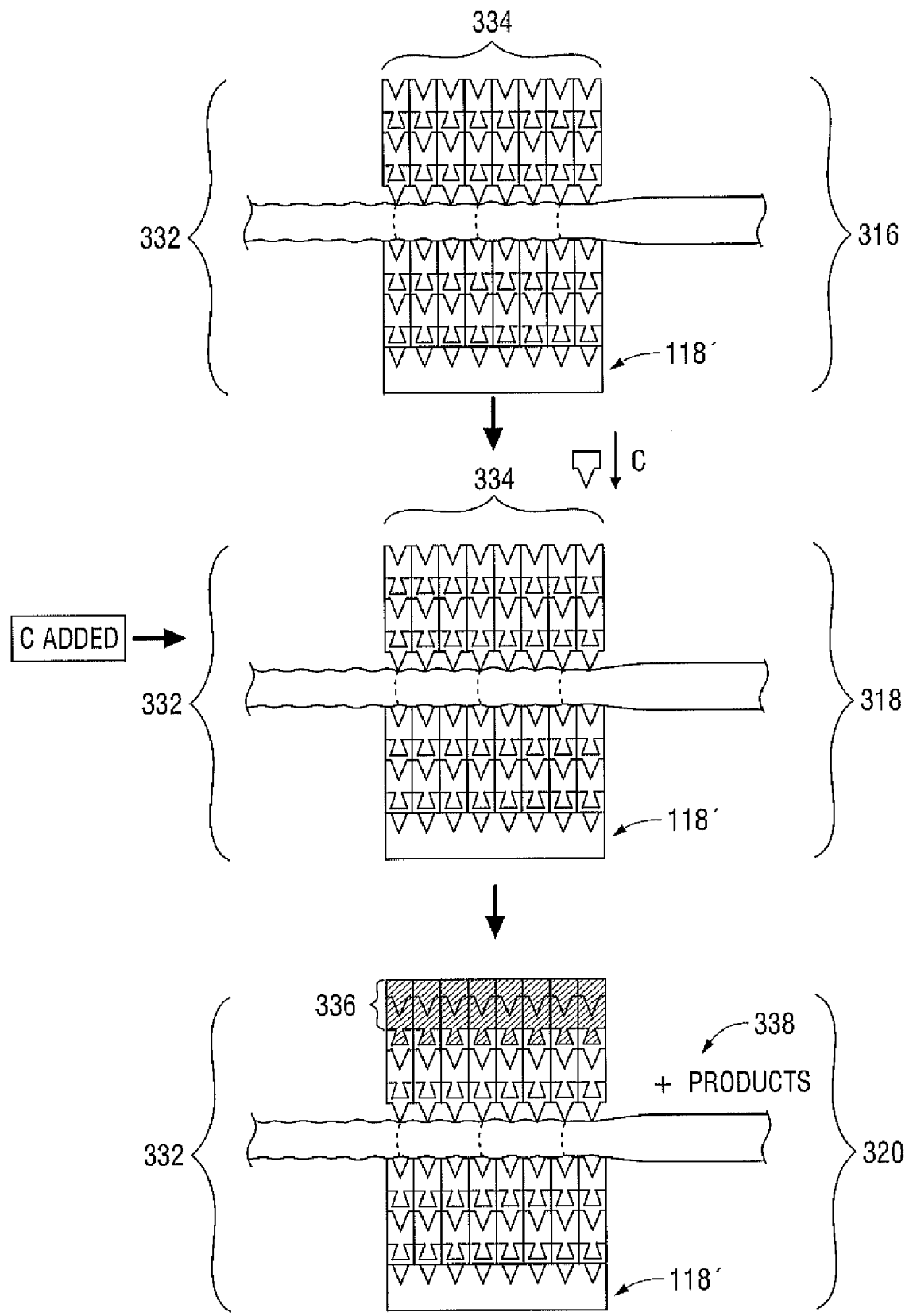

Referring to the drawings, FIGS. 3A-3B is an illustration 300 of various stages of disposing a coating on an electrode 118' using atomic layer deposition in accordance with an embodiment of the present disclosure. Illustration 300 includes stages 302 through 320. Stage 302 shows electrode 118' having a reacting surface 322. During stage 304 a precursor A is added. Precursor A reacts with reacting surface 322 resulting in electrode 118' as shown in stage 306. Precursor A reacts with reacting surface 322 forming a monolayer. The reactions occurring during stage 304 are self-limiting. Various molecules will be produced during the reaction and are represented as products 324. During stage 308, products 324 and excess A are flushed using a non-reacting gas.

In stage 310, a precursor B is added which reacts to surface 326. Stage 312 illustrates the results, that is, products 328 remain and electrode 118' has a reacting surface 330. Stage 214 flushes excess gases of precursor A and products 328. Note that stages 304 through 314 may be repeated several times. For example, stages 304 through 314 may be repeated until electrode 118' has a seed layer of a predetermined thickness. After a predetermined number of cycles, stage 316 shows the resulting electrode 118' with seed layer 332 having a reacting surface 334. Stage 218 adds precursor C, which thus reacts with reacting surface 334 forming the ALD layer 336 and products 338 as shown in stage 320. The ALD may be either hydrophobic or hydrophilic.

Figure 4:
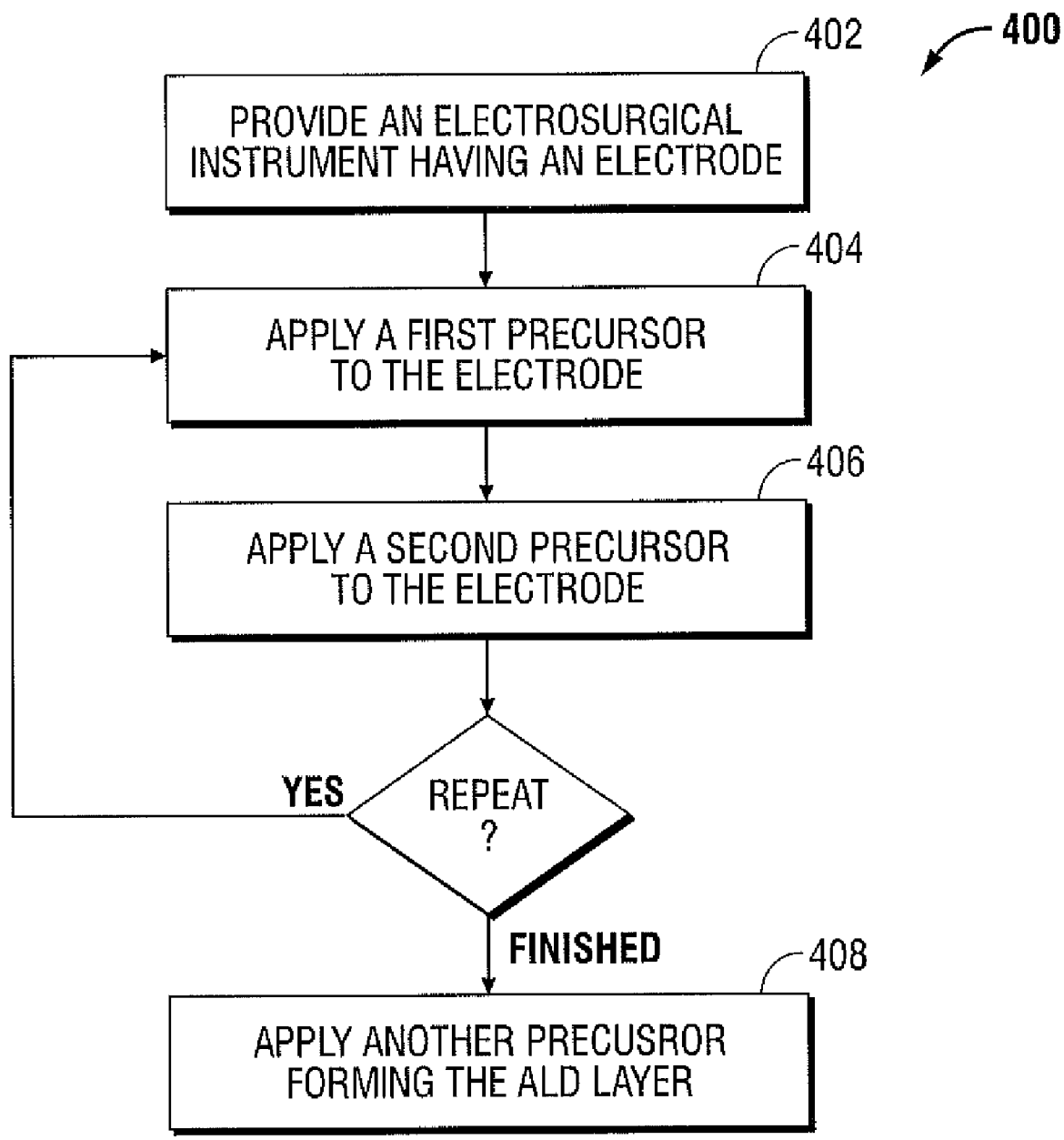
FIG. 4 is a flow chart diagram of a method of coating an electrode utilizing atomic layer deposition in accordance with an embodiment of the present disclosure.

Referring to the drawings, FIG. 4 is a flow chart of a method 400 of coating an electrode using utilizing atomic layer deposition in accordance with an embodiment of the present disclosure. Method 400 includes steps 402 through 408. Step 402 provides an electrosurgical instrument having an electrode. Step 404 applies a first precursor to the electrode. Step 406 applies a second precursor to the electrode. Steps 406 and 406 may be repeated as desired to control the thickness of the electrode coating. After the appropriate thickness of the seed layer is achieved, step 408 applies another precursor forming the ALD layer.

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An electrosurgical instrument, comprising:
   at least one support member;
   an electrode at least partially disposed on the at least one support member; and
   a coating at least partially disposed on the electrode comprising:
   a seed layer and an ALD layer, wherein the ALD layer is at least one of hydrophobic and hydrophilic and one of the seed layer or the ALD layer includes $Zn_{19}Al_5O_2$.

2. The electrosurgical instrument according to claim 1, wherein the seed layer is formed using atomic layer deposition.

3. The electrosurgical instrument according to claim 1, wherein the ALD layer comprises about 90% titania.

4. The electrosurgical instrument according to claim 1, wherein the ALD layer is formed from Tridecafluoro-1,1,2, 2-tetrahydrooctylmethyl-bis(dimethylamino)silane (FOMB (DMAS)S, $C_8F_{13}H_4(CH_3)Si(N(CH_2)_2)_2$).

5. A method of coating, comprising:
   providing an electrosurgical instrument, including:
      at least one support member; and
      an electrode at least partially disposed on the at least one support member;
   coating the electrode with a seed layer;
   coating the seed layer with an ALD layer, wherein the ALD layer is at least one of hydrophobic and hydrophilic and one of the seed layer or the ALD layer includes $Zn_{19}Al_5O_2$.

* * * * *